United States Patent [19]
Linsley et al.

[11] Patent Number: 5,434,131
[45] Date of Patent: Jul. 18, 1995

[54] CHIMERIC CTLA4 RECEPTOR AND METHODS FOR ITS USE

[75] Inventors: Peter S. Linsley; Jeffrey A. Ledbetter, both of Seattle; Nitin K. Damle, Renton; William Brady, Bothell, all of Wash.

[73] Assignee: Bristol Myers Squibb Co., Seattle, Wash.

[21] Appl. No.: 67,684

[22] Filed: May 26, 1993

Related U.S. Application Data

[62] Division of Ser. No. 723,617, Jun. 27, 1991, abandoned.

[51] Int. Cl.⁶ .................. A61K 38/17; A61K 39/395; C07K 14/725; C07K 19/00
[52] U.S. Cl. ........................................ 514/2; 514/12; 424/133.1; 530/350; 530/866; 530/868; 935/10
[58] Field of Search ............ 435/69.7; 530/386, 387.1, 530/387.3; 536/23.5; 935/10; 514/2; 424/85

[56] References Cited

U.S. PATENT DOCUMENTS

| | | | |
|---|---|---|---|
| 4,399,216 | 8/1983 | Axel et al. | 435/6 |
| 4,683,195 | 7/1987 | Mullis et al. | 435/6 |
| 4,683,202 | 7/1987 | Mullis | 435/91 |

OTHER PUBLICATIONS

J. Cohen Science 257:751 Aug. 7. 1992.
Janeway, "Approaching the Asymptote? Evolution and Revolution in Immunology", *Cold Spring Harbor Symp. Quant. Biol.* LIV:1–13 (1989).
Shaw and Shimuzu, "Two Molecular Pathways of Human T Cell Adhesion: Establishment of Receptor–Ligand Relationship", *Current Opinion in Immunology*, Eds. Kindt and Long, 1:92–97 (1988).
Hemler, "Adhesive Protein Receptors on Hematopoietic Cells", *Immunology Today* 9:109–113 (1988).
Kakiuchi et al., "B Cells as Antigen–Presenting Cells: The Requirement for B Cell Activation", *J. Immunol.* 131:109–114 (1983).
Krieger et al., "Antigen Presentation by Splenic B Cells: Resting B Cells are Ineffective, Whereas Activated B Cells are Effective Accessory Cells for T Cell Responses", *J. Immunol.* 135:2937–2945 (1985).
McKenzie, "Alloantigen Presentation by B Cells–Requirement for IL-1 and IL-6", *J. Immunol.* 141:2907–2911 (1988).
Hawrylowicz and Unanue, "Regulation of Antigen–Presentation-I IFN-γInduces Antigen–Presenting Properties on B Cells", *J. Immunol.* 141:4083–4088 (1988).
Springer et al., "The Lymphocyte Function-Associated LFA-1, CD2, and LFA-3 Molecules: Cell Adhesion Receptors of the Immune System", *A. Rev. Immunol.* 5:223–252 (1987).
Dinarello and Mier, "Current Concepts–Lymphokines", *New Engl. Jour. Med.* 317:940–945 (1987).
Weiss et al., "The Role of the T3/Antigen Receptor Complex in T-Cell Activation", *Ann. Rev. Immunol.* 4:593–619 (1986).
McMichael, Ed., "Non-Lineage, LFA-1 Family, and Leucocyte Common Antigens: New and Previously Defined Clusters", *Leukocyte Typing III*, Oxford Univ. Press, Oxford, UK (1987).
Moingeon et al., "CD2-mediated Adhesion Facilitates T Lymphocyte Antigen Recognition Function", *Nature* 339:312–314 (1988).
Makgoba et al., "ICAM-1 A Ligand for LFA-1-Dependent Adhesion of B, T and Myeloid Cells", *Nature* 331:86–88 (1988).

(List continued on next page.)

*Primary Examiner*—Garnette D. Draper
*Assistant Examiner*—Lorraine M. Spector
*Attorney, Agent, or Firm*—Merchant, Gould, Smith, Edell, Welter & Schmidt

[57] ABSTRACT

The invention identifies the CTLA4 receptor as a ligand for the B7 antigen. The complete amino acid sequence encoding human CTLA4 receptor gene is provided. Methods are provided for expressing CTLA4 as an immunoglobulin fusion protein, for preparing hybrid CTLA4 fusion proteins, and for using the soluble fusion proteins, fragments and derivatives thereof, including monoclonal antibodies reactive with B7 and CTLA4, to regulate T cell interactions and immune responses mediated by such interactions.

8 Claims, 10 Drawing Sheets

OTHER PUBLICATIONS

Staunton et al., "Functional Cloning of ICAM-2, A Cell Adhesion Ligand for LFA-1 Homologous to ICAM-1", *Nature* 339:61-64 (1989).

Norment et al., "Cell-Cell Adhesion Mediated by CD8 and MHC Class I Molecules", *Nature* 336:79-81 (1988).

Doyle and Strominger, "Interaction Between CD4 and Class II MHC Molecules Mediates Cell Adhesion", *Nature* 330:256-259 (1987).

Stoolman, "Adhesion Molecules Controlling Lymphocyte Migration", *Cell* 56:907-910 (1989).

Brescher and Cohn, "A Theory of Self-Nonself Discrimination", *Science* 169:1042-1049 (1970).

Freeman et al., "B7, A New Member of the Ig Superfamily with Unique Expression on Activated and Neoplastic B Cells", *J. Immunol.* 143(8):2714-2722 (1989).

Freedman et al., "B7, A B Cell-Restricted Antigen that Identifies Preactivated B Cells", *J. Immunol.* 138:3260-3267 (1987).

Clark et al., "Polypeptides on Human B Lymphocytes Associated with Cell Activation", *Human Immunol.* 16:100-113 (1986).

Yokochi et al., "B Lymphoblast Antigen (BB-1) Expressed on Epstein-Barr Virus-Activated B Cells Blasts, B Lymphoblastoid Cell Lines, and Burkitt's Lymphomas", *J. Immunol.* 128:823:827 (1981).

Weiss, "Structure and Function of the T Cell Antigen Receptor", *J. Clin. Invest.* 86:1015-1022 (1990).

Allen, "Antigen Processing at the Molecular Level", *Immunol. Today* 8:270-273 (1987).

Schwartz, "A Cell Culture Model for T Lymphocyte Clonal Anergy", *Science* 248:1349-1356 (1990).

Weaver and Unanue, "The Costimulatory Function of Antigen-Presenting Cells", *Immunol. Today* 11:49-55 (1990).

Aruffo and Seed, "Molecular Cloning of a CD28 cDNA by a High-Efficiency COS Cell Expression System", *Proc. Natl. Acad. Sci.* 84:8573-8577 (1987).

Damle et al., "Alloantigen-Specific Cytotoxic and Supressor T Lymphocytes are Derived from Phenotypically Distinct Precursors", *J. Immunol.* 131:2296-2300 (1983).

June et al., "T-Cell Proliferation Involving the CD28 Pathway is Associated with Cyclosporine-Resistant Interleukin 2 Gene Expression", *Mol. Cell. Biol.* 7:4472-4481 (1987).

Thompson et al., "CD28 Activation Pathway Regulates the Production of Multiple T-Cell-Derived Lymphokines/Cytokines", *Proc. Natl. Acad. Sci.* 86:1333-1337 (1989).

Lindsten et al. "Regulation of Lymphokine Messenger RNA Stability by a Surface-Mediated T Cell Activation Pathway", *Science* 244:339-343 (1989).

Damle et al., "Monoclonal Antibody Analysis of Human T Lymphocyte Subpopulations Exhibiting Autologous Mixed Lymphocyte Reaction", *Proc. Natl. Acad. Sci.* 78:5096-5098 (1981).

Lesslauer et al., "T90/44 (9.3 Antigen), A Cell Surface Molecule with a Function in Human T Cell Activation", *Eur. J. Immunol.* 16:1289-1296 (1986).

Linsley et al., "T-Cell Antigen CD28 Mediates Adhesion with B Cells by Interacting with Activation Antigen B7/BB-1", *Proc. Natl. Acad. Sci. USA*, 87:5031-5035 (1990).

Linsley et al., "Binding of the B Cell Activation Antigen B7 to CD28 Costimulates T Cell Proliferation and Interleukin 2 mRNA Accumulation", *J. Exp. Med.* 173:721-730 (1991).

Kohno et al., "CD28 Molecule as a Receptor-Like Function for Accessory Signals in Cell-Mediated Augmentation of IL-2 Production", *Cell Immunol.* 131:1-10 (1990).

Brunet et al., "A New Member of the Immunoglobulin Superfamily-CTLA-4", *Nature* 328:267-270 (1987).

Brunet et al., "A Differential Molecular Biology Search for Genes Preferentially Expressed in Functional T Lymphocytes: The CTLA Genes", *Immunol. Rev.* 103:21-36 (1988).

Dariavach et al., "Human Ig Superfamily CTLA-4 Gene: Chromosomal Localization and Identity of Protein Sequence Between Murine and Human CTLA-4 Cytoplasmic Domains," *Eur. J. Immunol.* 18:1901-1905 (1988).

Lafage-Pochitaloff et al., "Human CD28 and CTLA-4 Ig Superfamily Genes are Located on Chromosome 2 at Bands q33-q34", *Immunogenetics* 31:198-201 (1990).

Capon et al., "Designing CD4 Immunoadhesins for AIDS Therapy", *Nature* 337:525-531 (1989).

Malik et al., "Molecular Cloning, Sequence Analysis, and Functional Expression of a Novel Growth Regulator, Oncostatin M", *Molec. and Cell. Biol.* 9:2847-2853 (1989).

Storb, "Marrow Transplantation for Severe Aplastic (List continued on next page.)

OTHER PUBLICATIONS

Anemia: Methotrexate Alone Compared with a Combination of Methotrexate and Cyclosporine for Prevention of Acute Graft-Versus-Host Disease", *Blood* 56:119–125 (1986).

Storb and Thomas, "Graft-Versus-Host Disease in Dog and Man: The Seattle Experience", *Immunol. Rev.* 88:215–238 (1985).

Aruffo et al., "CD44 is the Principal Cell Surface Receptor for Hyaluronate", *Cell* 61:1303–1313 (1990).

Seed and Aruffo, "Molecular Cloning of the CD2 antigen, the T-cell Erythrocyte Receptor, by a Rapid Immunoselection Procedure", *Proc. Natl. Acad. Sci.* 84:3365–3369 (1987).

Aruffo and Seed, "Molecular Cloning of Two CD7 (T-Cell Leukemia Antigen) cDNAs by a COS Cell Expression System", *EMBO Hour,* 6:3313–3316 (1987).

Ledbetter et al., "Crosslinking of Surface Antigens Causes Mobilization of Intracellular Ionized Calcium in T Lymphocytes", *Proc. Natl. Acad. Sci.* 84:1384–1388 (1987).

Ledbetter et al., "CD28 Ligation in T-Cell Activation: Evidence for Two Signal Transduction Pathways", *Blood* 75:1531–1539 (1990).

Damle et al., "Immunoregulatory T Lymphocytes in Man", *J. Immunol.* 139:1501–1508 (1987).

Wysocki and Sato, "'Panning ' for Lymptocytes: A Method for Cell Selection", *Proc. Natl. Acad. Sci.* 75:2844–2848 (1978).

Damle et al., "Differential Regulatory Signals Delivered by Antibody Binding to the CD28 (Tp44) Molecule During the Activation of Human T Lymphocytes", *J. Immunol.* 140:1753–1761 (1988).

Schneck et al., "Inhibition of an Allospecific T Cell Hybridoma by Soluble Class I Proteins and Peptides: Estimation of the Affinity of a T Cell Receptor for MHC", *Cell* 56:47–55 (1989).

Recny et al., "Structural and Functional Characterization of the CD2 Immunoadhesion Domain", *J. Biol. Chem.* 265:8542–8549 (1990).

Clayton et al., "Identification of Human CD4 Residues Affecting Class II MHC Versis HIV-1 gp120 Binding", *Nature* 339:548–551 (1989).

Alzari et al., "Three-Dimensional Structure of Antibodies", *Ann. Rev. Immuno.* 6:555–580 (1988).

Hautanen et al., "Effects of Modifications of the RGD Sequence and Its Context on Recognition by the Fibronectin Receptor", *J. Biol. Chem.* 264:1437–1442 (1989).

DiMinno et al., "Exposure of Platelet Fibrinogen-Binding Sites by Collagen, Arachidonic Acid, and ADP:Inhibition by a Monoclonal Antibody to the Glycoprotein IIb-IIIa Complex", *Blood* 61:140–148 (1983).

Thiagarajan and Kelley, "Exposure of Binding Sites for Vitronectin on Platelets Following Stimulation", *J. Biol. Chem.* 263:3035–3038 (1988).

June et al., "Role of the CD28 Receptor in T-Cell Activation", *Immunology Today* 11:211–2316 (1989).

T. C. Pearson et al., Transplantation 57(12):1701–1706, Jun. 1994.

S. F. Bolling et al., J. Surgical Research 57:60–64, 1994.

P. M. Wallace et al., Transplantation 58(6):602–610, Sep. 15, 1994.

```
ONCOSTATIN M SIGNAL PEPTIDE
-25                          -20
 M   G   V   L   L   T   Q   R   T   L   L   S   L   V   L
ATG GGT GTA CTG CTC ACA CAG AGG ACG CTG CTC AGT CTG GTC CTT    45

-10                                    -1 +1
 A   L   L   F   P   S   M   A   S   M │ A   M   H   V   A
GCA CTC CTG TTT CCA AGC ATG GCG AGC ATG GCA ATG CAC GTG GCC    90

+10                                     +20
 Q   P   A   V   V   L   A   S   S   R   G   I   A   S   F
CAG CCT GCT GTG GTA CTG GCC AGC AGC CGA GGC ATC GCC AGC TTT   135

+30
 V   C   E   Y   A   S   P   G   K   A   T   E   V   R   V
GTG TGT GAG TAT GCA TCT CCA GGC AAA GCC ACT GAG GTC CGG GTG   180

+40                                    +50
 T   V   L   R   Q   A   D   S   Q   V   T   E   V   C   A
ACA GTG CTT CGG CAG GCT GAC AGC CAG GTG ACT GAA GTC TGT GCG   225

+60
 A   T   Y   M   M   G   N   E   L   T   F   L   D   D   S
GCA ACC TAC ATG ATG GGG AAT GAG TTG ACC TTC CTA GAT GAT TCC   270

+70                                    +80
 I   C   T   G   T   S   S   G   N   Q   V   N   L   T   I
ATC TGC ACG GGC ACC TCC AGT GGA AAT CAA GTG AAC CTC ACT ATC   315

+90
 Q   G   L   R   A   M   D   T   G   L   Y   I   C   K   V
CAA GGA CTG AGG GCC ATG GAC ACG GGA CTC TAC ATC TGC AAG GTG   360

GLYCOSYLATION SITE
             +100                                  +110
 E   L   M   Y   P   P   P   Y   Y   L   G   I   G │N   G
GAG CTC ATG TAC CCA CCG CCA TAC TAC CTG GGC ATA GGC AAC GGA   405

+120
 T │ Q   I   Y   V   I   D   P   E   P   C   P   D   S   D
ACC CAG ATT TAT GTA ATT GAT CCA GAA CCG TGC CCA GAT TCT GAC   450

+130
 F   L   L   W   I   L   A   A   V   S   S   G   L   F   F
TTC CTC CTC TGG ATC CTT GCA GCA GTT AGT TCG GGG TTG TTT TTT   495

+140                                   +150
 Y   S   F   L   L   T   A   V   S   L   S   K   M   L   K
TAT AGC TTT CTC CTC ACA GCT GTT TCT TTG AGC AAA ATG CTA AAG   540

+160
 K   R   S   P   L   T   T   G   V   Y   V   K   M   P   P
AAA AGA AGC CCT CTT ACA ACA GGG GTC TAT GTG AAA ATG CCC CCA   585

+170                                   +180
 T   E   P   E   C   E   K   Q   F   Q   P   Y   F   I   P
ACA GAG CCA GAA TGT GAA AAG CAA TTT CAG CCT TAT TTT ATT CCC   630

+187
 I   N
ATC AAT                                                       636
```

FIG. 3

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( C ) INDIVIDUAL ISOLATE: Homo sapiens ( x i ) SEQUENCE DESCRIPTION: SEQ ID NO:1:

CTAGCCACTG AAGCTTCACC ATGGGTGTAC TGCTCACAC                      3 9

( 2 ) INFORMATION FOR SEQ ID NO:2:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( C ) INDIVIDUAL ISOLATE: Homo sapiens ( x i ) SEQUENCE DESCRIPTION: SEQ ID NO:2:

TGGCATGGGC TCCTGATCAG GCTTAGAAGG TCCGGGAAA                      3 9

( 2 ) INFORMATION FOR SEQ ID NO:3:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( C ) INDIVIDUAL ISOLATE: Homo sapiens ( x i ) SEQUENCE DESCRIPTION: SEQ ID NO:3:

TTTGGGCTCC TGATCAGGAA AATGCTCTTG CTTGGTTGT                                      3 9

( 2 ) INFORMATION FOR SEQ ID NO:4:

( i ) SEQUENCE CHARACTERISTICS:
          ( A ) LENGTH: 84 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( C ) INDIVIDUAL ISOLATE: Homo sapiens ( x i ) SEQUENCE DESCRIPTION: SEQ ID NO:4:

AAGCAAGAGC ATTTTCCTGA TCAGGAGCCC AAATCTTCTG ACAAAACTCA CACATCCCCA              6 0

CCGTCCCCAG CACCTGAACT CCTG                                                     8 4

( 2 ) INFORMATION FOR SEQ ID NO:5:

( i ) SEQUENCE CHARACTERISTICS:
          ( A ) LENGTH: 41 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( C ) INDIVIDUAL ISOLATE: Homo sapiens ( x i ) SEQUENCE DESCRIPTION: SEQ ID NO:5:

CTTCGACCAG TCTAGAAGCA TCCTCGTGCG ACCGCGAGAG C                                  4 1

( 2 ) INFORMATION FOR SEQ ID NO:6:

( i ) SEQUENCE CHARACTERISTICS:
          ( A ) LENGTH: 47 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( C ) INDIVIDUAL ISOLATE: Homo sapiens ( x i ) SEQUENCE DESCRIPTION: SEQ ID NO:6:

CATTGCACAG TCAAGCTTCC ATGCCCATGG GTTCTCTGGC CACCTTG                            4 7

( 2 ) INFORMATION FOR SEQ ID NO:7:

( i ) SEQUENCE CHARACTERISTICS:
          ( A ) LENGTH: 39 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( C ) INDIVIDUAL ISOLATE: Homo sapiens ( x i ) SEQUENCE DESCRIPTION: SEQ ID NO:7:

ATCCACAGTG CAGTGATCAT TTGGATCCTG GCATGTGAC    39

( 2 ) INFORMATION FOR SEQ ID NO:8:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
    ( C ) INDIVIDUAL ISOLATE: Homo sapiens ( x i ) SEQUENCE DESCRIPTION: SEQ ID NO:8:

CTCAGTCTGG TCCTTGCACT CCTGTTTCCA AGCATGGCGA GCATGGCAAT GCACGTGGCC    60

CAGCC    65

( 2 ) INFORMATION FOR SEQ ID NO:9:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Homo sapiens ( x i ) SEQUENCE DESCRIPTION: SEQ ID NO:9:

TTTGGGCTCC TGATCAGAAT CTGGGCACGG TTG    33

( 2 ) INFORMATION FOR SEQ ID NO:10:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Homo sapiens ( x i ) SEQUENCE DESCRIPTION: SEQ ID NO:10:

CTAGCCACTG AAGCTTCACC AATGGGTGTA CTGCTCACAC AGAGGACGCT GCTCAGTCTG    60

GTCCTTGCAC TC    72

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Homo sapiens ( x i ) SEQUENCE DESCRIPTION: SEQ ID NO:11:

```
GCAATGCACG TGGCCCAGCC TGCTGTGGTA GTG                                    33
```

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Homo sapiens ( x i ) SEQUENCE DESCRIPTION: SEQ ID NO:12:

```
TGATGTAACA TGTCTAGATC AATTGATGGG AATAAAATAA GGCTG                       45
```

( 2 ) INFORMATION FOR SEQ ID NO:13:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Homo sapiens ( x i ) SEQUENCE DESCRIPTION: SEQ ID NO:13:

```
GCAATGCACG TGGCCCAGCC TGCTGTGGTA CTGGCCAGCA GCCGAGGCAT CGCCAGCTTT      60
GTGTGTGAGT ATGCATCTCC AGGCAAAGCC ACTGAGGTCC GGGTGACAGT GCTTCGGCAG     120
GCTGACAGCC AGGTGACTGA AGTCTGTGCG GCAACCTACA TGATGGGGAA TGAGTTGACC     180
TTCCTAGATG ATTCCATCTG CACGGGCACC TCCAGTGGAA ATCAAGTGAA CCTCACTATC     240
CAAGGACTGA GGGCCATGGA CACGGGACTC TACATCTGCA AGGTGGAGCT CATGTACCCA     300
CCGCCATACT ACCTGGGCAT AGGCAACGGA ACCCAGATTT ATGTAATTGA TCCAGAACCG     360
TGCCCAGATT CTGACTTCCT CCTCTGGATC CTTGCAGCAG TTAGTTCGGG GTTGTTTTTT     420
TATAGCTTTC TCCTCACAGC TGTTTCTTTG AGCAAAATGC TAAAGAAAAG AAGCCCTCTT     480
ACAACAGGGG TCTATGTGAA AATGCCCCCA ACAGAGCCAG AATGTGAAAA GCAATTTCAG     540
```

CCTTATTTTA TTCCCATCAA T        561

( 2 ) INFORMATION FOR SEQ ID NO:14:

( i ) SEQUENCE CHARACTERISTICS:
      ( A ) LENGTH: 187 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:14:

```
Ala Met His Val Ala Gln Pro Ala Val Val Leu Ala Ser Ser Arg Gly
 1           5                  10                  15
Ile Ala Ser Phe Val Cys Glu Tyr Ala Ser Pro Gly Lys Ala Thr Glu
            20                  25                  30
Val Arg Val Thr Val Leu Arg Gln Ala Asp Ser Gln Val Thr Glu Val
        35                  40                  45
Cys Ala Ala Thr Tyr Met Met Gly Asn Glu Leu Thr Phe Leu Asp Asp
    50                  55                  60
Ser Ile Cys Thr Gly Thr Ser Ser Gly Asn Gln Val Asn Leu Thr Ile
65                  70                  75                  80
Gln Gly Leu Arg Ala Met Asp Thr Gly Leu Tyr Ile Cys Lys Val Glu
                85                  90                  95
Leu Met Tyr Pro Pro Pro Tyr Tyr Leu Gly Ile Gly Asn Gly Thr Gln
                100                 105                 110
Ile Tyr Val Ile Asp Pro Glu Pro Cys Pro Asp Ser Asp Phe Leu Leu
        115                 120                 125
Trp Ile Leu Ala Ala Val Ser Ser Gly Leu Phe Phe Tyr Ser Phe Leu
    130                 135                 140
Leu Thr Ala Val Ser Leu Ser Lys Met Leu Lys Lys Arg Ser Pro Leu
145                 150                 155                 160
Thr Thr Gly Val Tyr Val Lys Met Pro Pro Thr Glu Pro Glu Cys Glu
                165                 170                 175
Lys Gln Phe Gln Pro Tyr Phe Ile Pro Ile Asn
                180                 185
```

CHIMERIC CTLA4 RECEPTOR AND METHODS FOR ITS USE

This application is a divisional of U.S. Ser. No. 723,617, filed Jun. 27, 1991, now abandoned the contents of which are hereby incorporated by reference.

FIELD OF THE INVENTION

The present invention relates to expression of the CTLA4 receptor gene, identification of the interaction between the receptor and cells expressing B7 antigen, and to methods for regulating cellular interactions involving the CTLA4 receptor.

BACKGROUND OF THE INVENTION

The hallmark of a vertebrate immune system is the ability to discriminate "self" from "non-self" (foreign). This property has led to the evolution of a system requiring multiple signals to achieve optimal immune activation (Janeway, *Cold Spring Harbor Symp. Quant. Biol.* 54:1–14 (1989)). T cell-B cell interactions are essential to the immune response. Levels of many cohesive molecules found on T cells and B cells increase during an immune response (Springer et al., (1987), supra; Shaw and Shimuzu, *Current Opinion in Immunology*, Eds. Kindt and Long, 1:92–97 (1988)); and Hemler *Immunology Today* 9:109–113 (1988)). Increased levels of these molecules may help explain why activated B cells are more effective at stimulating antigen-specific T cell proliferation than are resting B cells (Kaiuchi et al., *J. Immunol.* 131:109–114 (1983); Kreiger et al., *J. Immunol.* 135:2937–2945 (1985); McKenzie, *J. Immunol.* 141:2907–2911 (1988); and Hawrylowicz and Unanue, *J. Immunol.* 141:4083–4088 (1988)).

The generation of a T lymphocyte ("T cell") immune response is a complex process involving cell-cell interactions (Springer et al., *A. Rev. Immunol.* 5:223–252 (1987)), particularly between T and accessory cells such as B cells, and production of soluble immune mediators (cytokines or lymphokines) (Dinarello and Mier, *New Engl. Jour. Med.* 317:940–945 (1987)). This response is regulated by several T-cell surface receptors, including the T-cell receptor complex (Weiss et al., *Ann. Rev. Immunol.* 4:593–619 (1986)) and other "accessory" surface molecules (Springer et al., (1987) supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y. (1987)).

Antigen-independent intercellular interactions involving lymphocyte accessory molecules are essential for an immune response (Springer et al., (1987), supra). For example, binding of the T cell-associated protein, CD2, to its ligand LFA-3, a widely expressed glycoprotein (reviewed in Shaw and Shimuzu, supra), is important for optimizing antigen-specific T cell activation (Moingeon et al., *Nature* 339:314 (1988)). Another important adhesion system involves binding of the LFA-1 glycoprotein found on lymphocytes, macrophages, and granulocytes (Springer et al., (1987), supra; Shaw and Shimuzu (1988), supra) to its ligands ICAM-I (Makgoba et al., *Nature* 331:86–88 (1988)) and ICAM-2 (Staunton et al., *Nature* 339:61–64 (1989)). The T cell accessory molecules CD8 and CD4 strengthen T cell adhesion by interaction with MHC class I (Norment et al., *Nature* 336:79–81 (1988)) and class II (Doyle and Strominger, *Nature* 330:256–259 (1987)) molecules, respectively. "Homing receptors" are important for control of lymphocyte migration (Stoolman, *Cell* 56:907–910 (1989)). The VLA glycoproteins are integrins which appear to mediate lymphocyte functions requiring adhesion to extracellular matrix components (Hemler, supra). The CD2/LFA-3, LFA-1/ICAM-1 and ICAM-2, and VLA adhesion systems are distributed on a wide variety of cell types (Springer et al., (1987), supra; Shaw and Shimuzu, (1988,) supra and Hemler, (1988), supra).

It was proposed many years ago that B lymphocyte activation requires two signals (Bretscher and Cohn, *Science* 169:1042–1049 (1970)) and now it is believed that all lymphocytes require two signals for their optimal activation, an antigen specific or clonal signal, as well as a second, antigen nonspecific signal (Janeway, supra). Freeman et al. (*J. Immunol.* 143(8):2714–2722 (1989)) isolated and sequenced a cDNA clone encoding a B cell activation antigen recognized by mAb B7 (Freeman et al., *J. Immunol.* 138:3260 (1987)). COS cells transfected with this cDNA have been shown to stain by both labeled mAb B7 and mAb BB-1 (Clark et al., *Human Immunol.* 16:100–113 (1986); Yokochi et al., *J. Immunol.* 128:823 (1981)); Freeman et al., (1989) supra; and Freedman et al., (1987), supra)). In addition, expression of this antigen has been detected on cells of other lineages, such as monocytes (Freeman et al., supra).

The signals required for a T helper cell ($T_h$) antigenic response are provided by antigen-presenting cells (APC). The first signal is initiated by interaction of the T cell receptor complex (Weiss, *J. Clin. Invest.* 86:1015 (1990)) with antigen presented in the context of class II major histocompatibility complex (MHC) molecules on the APC (Allen, *Immunol. Today* 8:270 (1987)). This antigen-specific signal is not sufficient to generate a full response, and in the absence of a second signal may actually lead to clonal inactivation or anergy (Schwartz, *Science* 248:1349 (1990)). The requirement for a second "costimulatory" signal provided by the MHC has been demonstrated in a number of experimental systems (Schwartz, supra; Weaver and Unanue, *Immunol. Today* 11:49 (1990)). The molecular nature of these second signal(s) is not completely understood, although it is clear in some cases that both soluble molecules such as interleukin (IL)-1 (Weaver and Unanue, supra) and membrane receptors involved in intercellular adhesion (Springer, *Nature* 346:425 (1990)) can provide costimulatory signals.

CD28 antigen, a homodimeric glycoprotein of the immunoglobulin superfamily (Aruffo and Seed, *Proc. Natl. Acad. Sci.* 84:8573–8577 (1987)), is an accessory molecule found on most mature human T cells (Damle et al., *J. Immunol.* 131:2296–2300 (1983)). Current evidence suggests that this molecule functions in an alternative T cell activation pathway distinct from that initiated by the T-cell receptor complex (June et al., *Mol. Cell. Biol.* 7:4472–4481 (1987)). Monoclonal antibodies (mAbs) reactive with CD28 antigen can augment T cell responses initiated by various polyclonal stimuli (reviewed by June et al., supra). These stimulatory effects may result from mAb-induced cytokine production (Thompson et al., *Proc. Natl. Acad. Sci* 86:1333–1337 (1989); and Lindsten et al., *Science* 244:339–343 (1989)) as a consequence of increased mRNA stabilization (Lindsten et al., (1989), supra). Anti-CD28mAbs can also have inhibitory effects, i.e., they can block autologous mixed lymphocyte reactions (Damle et al., *Proc.*

Natl. Acad. Sci. 78:5096–6001 (1981)) and activation of antigen-specific T cell clones (Lesslauer et al., *Eur. J. Immunol.* 16:1289–1296 (1986)).

Studies have shown that CD28 is a counter-receptor for the B cell activation antigen, B7/BB-1 (Linsley et al, *Proc. Natl. Acad. Sci. USA* 87:5031–5035 (1990)). For convenience the B7/BB-1 antigen is hereafter referred to as the "B7 antigen". Interactions between CD28 and B7 antigen have been characterized using genetic fusions of the extracellular portions of B7 antigen and CD28 receptor, and Immunoglobulin (Ig) Cγ1 (constant region heavy chains) (Linsley et al, *J. Exp. Med.* 173:721–730 (1991)). Immobilized B7Ig fusion protein, as well as B7 positive CHO cells, have been shown to costimulate T cell proliferation. T cell stimulation with B7 positive CHO cells also specifically stimulates increased levels of transcripts for IL-2. Additional studies have shown that anti-CD28 mAb inhibited IL-2 production induced in certain T cell leukemia cell lines by cellular interactions with a B cell leukemia line (Kohno et al., *Cell. Immunol.* 131-1-10 (1990)).

CD28 has a single extracellular variable region (V)-like domain (Aruffo and Seed, supra). A homologous molecule, CTLA4 has been identified by differential screening of a murine cytolytic-T cell cDNA library (Brunet et al., *Nature* 328:267–270 (1987)). Transcripts for this molecule have been found in T cell populations having cytotoxic activity, suggesting that CTLA4 might function in the cytolytic response (Brunet et al., supra; and Brunet et al., *Immunol. Rev.* 103-21-36 (1988)). Researchers have reported the cloning and mapping of a gene for the human counterpart of CTLA4 (Dariavach et al., *Eur. J. Immunol.* 18:1901–1905 (1988)) to the same chromosomal region (2q33-34) as CD28 (Lafage-Pochitaloff et al., *Immunogenetics* 31:198–201 (1990)). Sequence comparison between this human CTLA4 DNA and that encoding CD28 proteins reveals significant homology of sequence, with the greatest degree of homology in the juxtamembrane and cytoplasmic regions (Brunet et al., 1988, supra; Dariavach et al., 1988, supra).

The high degree of homology between CD28 and CTLA4, together with the co-localization of their genes, raises questions as to whether these molecules are also functionally related. However, since the protein product of CTLA4 has not yet been successfully expressed, these questions remain unanswered.

Expression of soluble derivatives of cell-surface glycoproteins in the immunoglobulin gene superfamily has been achieved for CD4, the receptor for HIV-1, and CD28 and B7 receptors, using hybrid fusion molecules consisting of DNA sequences encoding amino acids corresponding to portions of the extracellular domain of CD4 receptor fused to antibody domains (immunoglobulin γ1 (Capon et al., *Nature* 337:525–531 (1989) (CD4) and Linsley et al., *J. Exp. Med.*, supra (CD28 and B7)).

It would be useful to obtain expression of a soluble protein product of the heretofore unexpressed CTLA4 gene, and to identify a natural ligand for CTLA4 that is involved in functional responses of T cells. The soluble protein product could then be used to regulate T cell responses in vivo to treat pathological conditions.

SUMMARY OF THE INVENTION

Accordingly, the present invention provides the complete and correct DNA sequence encoding the amino acid sequence corresponding to the CTLA4 receptor protein, and identifies B7 antigen as a natural ligand for the CTLA4 receptor. The invention also provides a method for expressing the DNA as a CTLA4 immunoglobulin (Ig) fusion protein product. Embodiments of the invention include CTLA4Ig fusion protein, and hybrid fusion proteins including CD28Ig/CTLA4Ig fusion proteins. Also provided are methods for using the CTLA4 fusion protein, B7Ig fusion protein, hybrid fusion proteins, and fragments and/or derivatives thereof, such as monoclonal antibodies reactive with CTLA4 and the B7 antigen, to regulate cellular interactions and immune responses.

The human CTLA receptor protein of the invention is encoded by 187 amino acids and includes a newly identified N-linked glycosylation site.

The CTLA4Ig fusion protein of the invention binds the B7 antigen expressed on activated B cells, and cells of other lineages, a ligand for CD28 receptor on T cells. The CTLA4Ig binds B7 antigen with significantly higher affinity than B7 binding to the CD28 receptor. The CTLA4Ig construct has a first amino acid sequence corresponding to the extracellular domain of the CTLA4 receptor fused to a second amino acid sequence corresponding to the human Ig Cγ1 domain. The first amino acid sequence contains amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgCγ1. The fusion protein is preferably produced in dimeric form. Soluble CTLA4Ig is a potent inhibitor in vitro of T and B lymphocyte responses.

Also contemplated in the invention are hybrid fusion proteins such as CD28Ig/CTLA4Ig fusion proteins having a first amino acid sequence corresponding to fragments of the extracellular domain of CD28 joined to a second amino acid sequence corresponding to fragments of the extracellular domain of CTLA4Ig and a third amino acid sequence corresponding to the hinge, CH2 and CH3 regions of human IgCγ1. One embodiment of the hybrid fusion proteins is a CD28Ig/CTLA4Ig fusion construct having a first amino acid sequence containing amino acid residues from about position 1 to about position 94 of the amino acid sequence corresponding to the extracellular domain of CD28, joined a second amino acid sequence containing amino acid residues from about position 94 to about position 125 of the amino acid sequence corresponding to the extracellular domain of CTLA4, joined to a third amino acid sequence containing amino acids residues corresponding to the hinge, CH2 and CH3 regions of human IgCγ1.

Also included in the invention is a method for regulating T cell interactions with other cells by inhibiting the interaction of CTLA4-positive T cells with B7 positive cells by reacting the T cells with ligands for the CTLA4 receptor. The ligands include B7Ig fusion protein, a monoclonal antibody reactive with CTLA4 receptor, and antibody fragments.

The invention also provides a method for regulating T cell interactions with B7 positive cells, using a ligand for the B7 antigen. Such a ligand is the CTLA4Ig fusion protein of the invention, its fragments or derivatives, the CD28Ig/CTLA4Ig fusion protein hybrid, or a monoclonal antibody reactive with the B7 antigen.

The invention further includes a method for treating immune system diseases mediated by T cell interactions with B7 positive cells by administering a ligand reactive with B7 antigen to regulate T cell interactions with B7 positive cells. The ligand is the CTLA4Ig fusion protein, or the CD28Ig/CTLA4Ig fusion protein hybrid, or a monoclonal antibody reactive with B7 antigen.

A monoclonal antibody reactive with the CTLA4Ig fusion protein and a monoclonal antibody reactive with CD28Ig/CTLA4Ig fusion protein are described for use in regulating cellular interactions.

A novel Chinese Hamster Ovary cell line stably expressing the CTLA4Ig fusion protein is also disclosed.

BRIEF DESCRIPTION OF THE DRAWINGS

FIG. 3 depicts the complete amino acid sequence encoding human CTLA4 receptor (SEQ ID NOs: 13 and 14) fused to the oncostatin M signal peptide (position −25 to −1), and including the newly identified N-linked glycosylation site (position 109-111), as described in Example 3, infra.

DETAILED DESCRIPTION OF THE INVENTION

Figure 1:
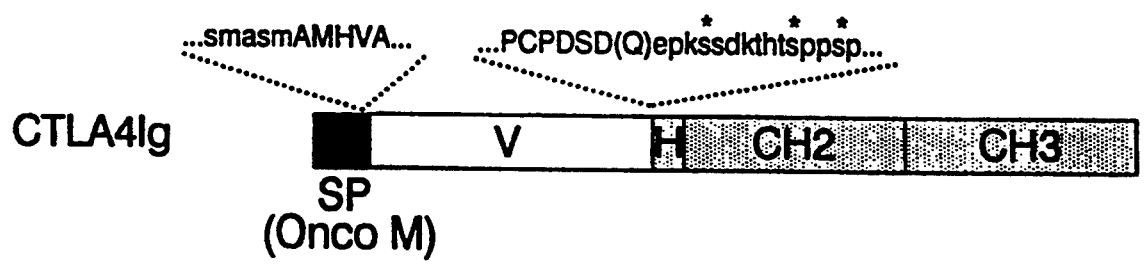
FIG. 1 is a diagrammatic representation of CTLA4Ig fusion constructs as described in Example 2, infra.

In order that the invention herein described may be more fully understood, the following description is set forth.

This invention is directed to the isolation and expression of the human CTLA4 receptor found on T cell surfaces, which binds to the B7 antigen expressed on activated B cells, and cells of other lineages, and to expression of soluble fusion protein products of the CTLA4 receptor gene. The invention also provides methods for using the expressed CTLA4 receptor to regulate cellular interactions, including T cell interactions with B7 positive cells.

In a preferred embodiment, the complete and correct DNA sequence encoding the amino acid sequence corresponding to human CTLA4 receptor protein of the invention is cloned using PCR. The cDNA containing the complete predicted coding sequence of CTLA4 was assembled from two PCR fragments amplified from H38 RNA, and inserted into the expression vector, CDM8 as described in detail in the Examples, infra. Isolates were transfected into COS cells and tested for binding of B7Ig, a soluble fusion protein having an amino acid sequence corresponding to the extracellular domain of B7 and a human immunoglobulin (Ig) Cγ1 region, as described by Linsley et al., *J. Exp. Med.* 173:721–730 (1991).

The DNA sequence of one isolate, designated as OMCTLA4, was then determined and found to correspond exactly to the predicted human CTLA4 sequence, fused at the N-terminus to the signal peptide from oncostatin M. The CTLA4 receptor is encoded by 187 amino acids (exclusive of the signal peptide and stop codons) and includes a newly identified N-linked glycosylation site at amino acid positions 109-111 (see FIG. 3, infra). The CTLA4 receptor is expressed using the oncostatin M signal peptide.

In another preferred embodiment, soluble forms of the protein product of the CTLA4 receptor gene (CTLA4Ig) are prepared using fusion proteins having a first amino acid sequence corresponding to the extracellular domain of CTLA4 and a second amino acid sequence corresponding to the human IgCγ1 domain. Cloning and expression plasmids (CDM8 and πLN) were constructed containing cDNAs encoding portions of the amino acid sequence corresponding to human CTLA4 receptor based on the cDNA sequence described herein, where the cDNA encoding a first amino acid sequence corresponding to a fragment of the extracellular domain of the CTLA4 receptor gene is joined to DNA encoding a second amino acid sequence corresponding to an IgC region that permits the expression of the CTLA4 receptor gene by altering the solubility of the expressed CTLA4 protein. Thus, soluble CTLA4Ig fusion protein is encoded by a first amino acid sequence containing amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgCγ1. The fusion protein is preferably produced in dimeric form. The construct was then transfected into COS or CHO cells, and CTLA4Ig was purified and identified as a dimer.

DNA encoding the amino acid sequence corresponding to the CTLA4Ig fusion protein has been deposited with the American Type Culture Collection (ATCC) in Rockville, Md., under the provisions of the Budapest Treaty on May 31, 1991 and has been accorded ATCC accession number: 68629.

The present invention provides the first protein product of CTLA4 transcripts in the form of a soluble fusion protein. The CTLA4Ig protein forms a disulfide-linked dimer of $M_r$ of approximately 50,000 subunits, indicating that native CTLA4 probably exists on the T cell surface as a disulfide-linked homodimer.

B7 antigen has been shown to be a ligand for CD28 receptor on T cells (Linsley et al., *Proc. Natl. Acad. Sci. USA*, supra). The CTLA4 receptor molecule appears functionally and structurally related to the CD28 receptor; both are receptors for the B cell activation antigen, B7, while CTLA4 appears to have higher affinity for B7, among the highest yet reported for lymphoid adhesion systems. However, CTLA4Ig was shown to bind more strongly to B7 positive (B7+) cell lines than CD28Ig. Other experiments demonstrated that CTLA4 is a higher affinity receptor for B7 antigen than CD28 receptor. Additionally, CTLA4Ig was shown to bind a single protein on lymphoblastoid cells which is similar in size to the B7 antigen. CTLA4Ig inhibited T cell proliferation and inhibited $T_h$-induced IgM production.

In another preferred embodiment, hybrid fusion proteins having amino acid sequences corresponding to fragments of different receptor proteins were constructed. For example, amino acid sequences corresponding to selected fragments of the extracellular domains of CD28 and CTLA4 were linked to form CD28Ig/CTLA4Ig hybrid fusion proteins. Thus, a CD28Ig/CTLA4Ig fusion protein was obtained having a first amino acid sequence containing amino acid residues corresponding to a fragment of the extracellular domain of CD28 joined to a second amino acid sequence corresponding to a fragment of the extracellular domain of CTLA4Ig and to a third amino acid sequence corresponding to the hinge, CH2 and CH3 regions of human IgCγ1. One embodiment of the hybrid fusion proteins is a CD28Ig/CTLA4Ig fusion construct having a first amino acid sequence containing amino acid residues from about position 1 to about position 94 of the amino acid sequence corresponding to the extracellular domain of CD28, joined to a second amino acid sequence containing amino acid residues from about position 94 to about position 125 of the amino acid sequence corresponding to the extracellular domain of CTLA4, joined to a third amino acid sequence corresponding to the hinge, CH2 and CH3 regions of human IgCγ1.

The techniques for cloning and expressing DNA sequences encoding the amino acid sequences corresponding to the CTLA4 receptor protein, soluble fusion proteins and hybrid fusion proteins, e.g. synthesis of oligonucleotides, PCR, transforming cells, constructing vectors, expression systems, and the like are well-established in the art, and most practitioners are familiar with the standard resource materials for specific conditions and procedures. However, the following paragraphs are provided for convenience and notation of modifications where necessary, and may serve as a guideline.

Cloning and Expression of Coding Sequences for Receptors and Fusion Proteins

Fusion protein constructs corresponding to CD28IgCγ1 and B7IgCγ1 for characterizing the CTLA4Ig of the present invention, and for preparing CD28Ig/CTLA4Ig fusion hybrids, were prepared as described by Linsley et al., *J. Exp. Med.* 173:721-730 (1991), incorporated by reference herein. Alternatively, cDNA clones may be prepared from RNA obtained from cells expressing B7 antigen and CD28 receptor based on knowledge of the published sequences for these proteins (Aruffo and Seed, and Freeman, supra) using standard procedures.

CTLA4Ig fusions consisting of DNA encoding amino acid sequences corresponding to the extracellular domain of CTLA4 and the hinge, CH2 and CH3 regions of human IgCγ1 were constructed by ligation of PCR fragments. The cDNA encoding the amino acid sequences is amplified using the polymerase chain reaction ("PCR") technique (see U.S. Pat. Nos. 4,683,195 and 4,683,202 to Mullis et al. and Mullis & Faloona, *Methods Enzymol.* 154:335-350 (1987)). CTLA4Ig fusion polypeptides were obtained having DNA encoding amino acid sequences containing amino acid residues from about position 1 to about position 125 of the amino acid sequence corresponding to the extracellular domain of CTLA4 and DNA encoding amino acid sequences corresponding to the hinge, CH2 and CH3 regions of Ig Cγ1.

Because the expression of CTLA4 receptor protein in human lymphoid cells has not been previously reported, it was necessary to locate a source of CTLA4 mRNA. PCR cDNA made from the total cellular RNA of several human leukemia-cell lines was screened, using as primers, oligonucleotides from the published sequence of the CTLA4 gene (Dariavach et al., supra). Of the cDNA tested, H38 cells (an HTLV II-associated leukemia line) provided the best yield of PCR products having the expected size. Since a signal peptide for CTLA4 was not identified in the CTLA4 gene, the N terminus of the predicted sequence of CTLA4 was fused to the signal peptide of oncostatin M (Malik et al., *Molec. and Cell. Biol.* 9:2847 (1989)) in two steps using oligonucleotides as described in the Examples, infra. The product of the PCR reaction was ligated with cDNA encoding the amino acid sequences corresponding to the hinge, CH2 and CH3 regions Of Ig Cγ1 into a expression vector, such as CDM8 or πLN.

To obtain DNA encoding full length human CTLA4, a cDNA encoding the transmembrane and cytoplasmic domains of CTLA4 was obtained by PCR from H38 cells and joined with a fragment from CTLA4Ig, obtained as described above, encoding the oncostatin M signal peptide fused to the N terminus of CTLA4, using oligonucleotide primers as described in the Examples, infra. PCR fragments were ligated into the plasmid CDM8, resulting in an expression plasmid encoding the full length CTLA4 gene, and designated OMCTLA4.

For construction of DNA encoding the amino acid sequence corresponding to hybrid fusion proteins, DNA encoding amino acids corresponding to portions of the extracellular domain of one receptor gene is joined to DNA encoding amino acids corresponding to portions of the extracellular domain of another receptor gene, and to DNA encoding the amino acid sequences corresponding to the hinge, CH2 and CH3 regions of human IgCγ1 using procedures as described above for the B7Ig, CD28Ig and CTLA4Ig constructs. Thus, for example, DNA encoding amino acid residues from about position 1 to about position 94 of the amino acid sequence corresponding to the extracellular domain of the CD28 receptor is joined to DNA encoding amino acid residues from about position 94 to about position 125 of the amino acid sequence corresponding to the extracellular domain of the CTLA4 receptor and to DNA encoding the amino acid sequences corresponding to the hinge, CH2 and CH3 regions of human IgCγ1.

To produce large quantities of cloned DNA, vectors containing DNA encoding the fusion constructs of the invention are transformed into suitable host cells, such as the bacterial cell line E. coli strain MCt061/p3 (Invitrogen Corp., San Diego, Calif.) using standard procedures, and colonies are screened for the appropriate plasmids.

The clones containing DNA encoding fusion constructs obtained as described above are then transfected into suitable host cells for expression. Depending on the host cell used, transfection is performed using standard techniques appropriate to such cells. For example, transfection into mammalian cells is accomplished using DEAE-dextran mediated transfection, CaPO4 co-precipitation, lipofection, electroporation, or protoplast fusion, and other methods known in the art including:

lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression in eukaryotic host cell cultures derived from multicellular organisms is preferred (see *Tissue Cultures*, Academic Press, Cruz and Patterson, Eds. (1973)). These systems have the additional advantage of the ability to splice out introns and thus can be used directly to express genomic fragments. Useful host cell lines include Chinese hamster ovary (CHO), monkey kidney (COS), VERO and HeLa cells. In the present invention, cell lines stably expressing the fusion constructs are preferred.

Expression vectors for such cells ordinarily include promoters and control sequences compatible with mammalian cells such as, for example, CMV promoter (CDM8 vector) and arian sarcoma virus (ASV) ($\pi$LN vector). Other commonly used early and late promoters include those from Simian Virus 40 (SV 40) (Fiers, et al., *Nature* 273:113 (1973)), or other viral promoters such as those derived from polyoma, Adenovirus 2, and bovine papilloma virus. The controllable promoter, hMTII (Karin, et al., *Nature* 299:797-802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eukaryotes.

Although preferred host cells for expression of the fusion constructs include eukaryotic cells such as COS or CHO cells, other eukaryotic microbes may be used as hosts. Laboratory strains of Saccharomyces cerevisiae, Baker's yeast, are most used although other strains such as Schizosaccharomyces pombe may be used. Vectors employing, for example, the 2$\mu$ origin of replication of Broach, *Meth. Enz.* 101:307 (1983), or other yeast compatible origins of replications (see, for example, Stinchcomb et al., *Nature* 282:39 (1979)); Tschempe et al., *Gene* 10:157 (1980); and Clarke et al., *Meth. Enz.* 101:300 (1983)) may be used. Control sequences for yeast vectors include promoters for the synthesis of glycolytic enzymes (Hess et al., *J. Adv. Enzyme Req.* 7:149 (1968); Holland et al., *Biochemistry* 17:4900 (1978)). Additional promoters known in the art include the CMV promoter provided in the CDM8 vector (Toyama and Okayama, *FEBS* 268:217-221 (1990); the promoter for 3-phosphoglycerate kinase (Hitzeman et al., *J. Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198: 1056 (1977)), the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

The nucleotide sequences encoding CD28Ig and CTLA4Ig proteins, and fusion hybrid proteins such as CD28Ig/CTLA4Ig, may be expressed in a variety of systems as set forth below. The cDNA may be excised by suitable restriction enzymes and ligated into suitable prokaryotic or eukaryotic expression vectors for such expression. Because CD28 and CTLA4 receptor proteins occur in nature as dimers, it is believed that successful expression of these proteins requires an expression system which permits these proteins to form as dimers. Truncated versions of these proteins (i.e. formed by introduction of a stop codon into the sequence at a position upstream of the transmembrane region of the protein) appear not to be expressed. The expression of CD28 and CTLA4 receptors as fusion proteins permits dimer formation of these proteins. Thus, expression of CTLA4 protein as a fusion product is preferred in the present invention.

A stable CHO line of the invention, designated Chinese Hamster Ovary Cell Line CTLA4Ig-24, is preferred for expression of CTLA4Ig and has been deposited with the ATCC under the terms of the Budapest Treaty on May 31, 1991, and accorded ATCC accession number 10762.

Expression of the CTLA4 receptor of the invention is accomplished transfecting a cell line such as COS cells, and detecting expression by binding of the CTLA4-transfected cells to a ligand for the CTLA4 receptor, for example by testing for binding of the cells to B7Ig fusion protein.

Sequences of the resulting constructs are confirmed by DNA sequencing using known procedures, for example as described by Sanger et al., *Proc. Natl. Acad. Sci. USA* 74:5463 (1977), as further described by Messing et al., *Nucleic Acids Res.* 9:309 (1981), or by the method of Maxam et al. *Methods Enzymol.* 65:499 (1980)).

Recovery of Protein Products

As noted above, CD28 and CTLA4 receptor genes are not readily expressed as mature proteins using direct expression of DNA encoding the truncated protein. To enable homodimer formation, DNA encoding the amino acid sequence corresponding to the extracellular domains of CD28 and CTLA4, and including the codons for a signal sequence such as that of oncostatin M in cells capable of appropriate processing, is fused with DNA encoding the amino acid sequence corresponding to the Fc domain of a naturally dimeric protein. Purification of these fusion protein products after secretion from the cells is thus facilitated using antibodies reactive with the anti-immunoglobulin portion of the fusion proteins. When secreted into the medium, the fusion protein product is recovered using standard protein purification techniques, for example by application to protein A columns.

USE

CTLA4Ig fusion protein and/or fragments of the fusion protein may be used to react with B7 positive cells, such as B cells, to regulate immune responses mediated by T cell interactions with the B7 antigen positive cells.

CTLA4Ig fusion protein and CTLA4Ig/CD28Ig hybrid proteins, and/or fragments and derivatives of these proteins, may also be used to react with B7 positive cells, including B cells, to regulate immune responses mediated by T cell dependent B cell responses. The term "fragment" as used herein means a portion of the amino acid sequence encoding the protein referred to as "CTLA4". A fragment of the CTLA4Ig fusion protein that may be used is a polypeptide having an amino acid sequence corresponding to some portion of the amino acid sequence corresponding to the CTLA4 receptor used to obtain the CTLA4Ig fusion protein as described herein.

The B7 antigen expressed on activated B cells and cells of other lineages, and the CD28 receptor expressed on T cells, can directly bind to each other, and this interaction can mediate cell-cell interaction. Such interactions directly trigger the CD28 activation pathway in T cells, leading to cytokine production, T cell proliferation, and B cell differentiation into immunoglobulin producing cells. The activation of B cells that occurs, can cause increased expression of B7 antigen and further CD28 stimulation, leading to a state of chronic inflammation such as in autoimmune diseases, altograft rejection, graft versus host disease or chronic allergic reactions. Blocking or inhibiting this reaction may be effective in preventing T cell cytokine production and thus preventing or reversing inflammatory reactions.

CTLA4Ig is shown herein to be a potent inhibitor of in vitro lymphocyte functions requiring T and B cell interaction. This indicates the importance of interactions between the B7 antigen and its counter-receptors, CTLA4 and/or CD28. The cytoplasmic domains of murine and human CTLA4 are similar (Dariavach et al., supra, 1988), suggesting that this region has important functional properties. The cytoplasmic domains of CD28 and CTLA4 also share homology.

CTLA4 is a more potent inhibitor in vitro of lymphocyte responses than either anti-BB1, or anti-CD28 mAbs. CTLA4Ig does not have direct stimulatory effects on T cell proliferation to counteract its inhibitory effects. Therefore, the CTLA4Ig fusion protein may perform as a better inhibitor in vivo than anti-CD28 monoclonal antibodies. The immunosuppressive effects of CTLA4Ig in vitro suggests its use in therapy for treatment of autoimmune disorders involving abnormal T cell activation or Ig production.

The CTLA4Ig fusion protein is expected to exhibit inhibitory properties in vivo. Thus, it is expected that CTLA4Ig will act to inhibit T cells in a manner similar to the effects observed for the anti-CD28 antibody, under similar conditions in vivo. Under conditions where T cell/B cell interactions are occurring as a result of contact between T cells and B cells, binding of introduced CTLA4Ig to react with B7 antigen positive cells, for example B cells, may interfere, i.e. inhibit, the T cell/B cell interactions resulting in regulation of immune responses. Because of this exclusively inhibitory effect, CTLA4Ig is expected to be useful in vivo as an inhibitor of T cell activity, over non-specific inhibitors such as cyclosporine and glucosteroids.

In one embodiment, the CTLA4Ig fusion protein or CTLA4Ig/CD28Ig hybrid proteins, may be introduced in a suitable pharmaceutical carrier in vivo, i.e. administered into a human subject for treatment of pathological conditions such as immune system diseases or cancer. Introduction of the fusion protein in vivo is expected to result in interference with T cell interactions with other cells, such as B cells, as a result of binding of the ligand to B7 positive cells. The prevention of normal T cell interactions may result in decreased T cell activity, for example, decreased T cell proliferation. In addition, administration of the fusion protein in vivo is expected to result in regulation of in vivo levels of cytokines, including, but not limited to, interleukins, e.g. interleukin ("IL")-2, IL-3, IL-4, IL-6, IL-8, growth factors including tumor growth factor ("TGF"), colony stimulating factor ("CSF"), interferons ("IFNs"), and tumor necrosis factor ("TNF") to promote desired effects in a subject. For example, when the fusion protein is introduced in vivo, it may block production of cytokines, which contribute to malignant growth, for example of tumor cells. The fusion protein may also block proliferation of viruses dependent on T cell activation, such as the virus that causes AIDS, HTLV1.

Under some circumstances, as noted above, the effect of administration of the CTLA4Ig fusion protein or its fragments in vivo is inhibitory, resulting from blocking by the fusion protein of the CTLA4 and CD28 triggering resulting from T cell/B cell contact. For example, the CTLA4Ig protein may block T cell proliferation. Introduction of the CTLA4Ig fusion protein in vivo will thus produce effects on both T and B cell-mediated immune responses. The fusion protein may also be administered to a subject in combination with the introduction of cytokines or other therapeutic reagents.

In an additional embodiment of the invention, other reagents, including derivatives reactive with the CTLA4Ig fusion protein or the CTLA4 receptor are used to regulate T cell interactions. For example, antibodies, and/or antibody fragments reactive with the CTLA4 receptor may be screened to identify those capable of inhibiting the binding of the CTLA4Ig fusion protein to the B7 antigen. The antibodies or antibody fragments such as Fab or F(ab')$_2$ fragments, may then be used to react with the T cells, for example, to inhibit T cell proliferation.

Monoclonal antibodies reactive with CTLA4 receptor, may be produced by hybridomas prepared using known procedures, such as those introduced by Kohler and Milsrein (see Kohler and Milsrein, Nature, 256:495-97 (1975))., and modifications thereof, to regulate cellular interactions.

These techniques involve the use of an animal which is primed to produce a particular antibody. The animal can be primed by injection of an immunogen (e.g. the B7Ig fusion protein, CTLA4Ig fusion protein or CD28Ig/CTLA4Ig hybrid fusion protein) to elicit the desired immune response, i.e. production of antibodies from the primed animal. A primed animal is also one which is expressing a disease. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the CTLA4Ig protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (see Zola et al., in *Monoclonal Hybridoma Antibodies: Techniques and Applications,* Hurell (ed.) pp. 51-52 (CRC Press, 1982)). Hybridomas produced according to these methods can be propagated in vitro or in vivo (in ascites fluid) using techniques known in the art (see generally Fink et al., *Prog. Clin. Pathol.,* 9:121-33 (1984), FIG. 6-1 at p. 123).

Generally, the individual cell line may be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region reactive with the extracellular domain of CTLA4 receptor, such as Fab, F(ab')$_2$ and Fv fragments may be produced. Such fragments can be produced using techniques well established in the art (see e.g. Rousseaux et al., in *Methods Enzymol.,* 121:663-69, Academic Press (1986)).

Anti-B7 monoclonal antibodies prepared as described above may be used to bind to B7 antigen to inhibit interactions of CD28-positive or CTLA4-positive T cells with B7 positive cells. Anti-CTLA4 monoclonal antibodies may be used to bind to CTLA4 receptor to inhibit the interaction of CTLA4-positive T cells with other cells.

In another embodiment, the CTLA4Ig fusion protein may be used to identify additional compounds capable of regulating the interaction between CTLA4 and the B7 antigen. Such compounds may include small naturally occurring molecules that can be used to react with B cells and/or T cells. For example, fermentation broths may be tested for the ability to inhibit CTLA4/B7 interactions. In addition, derivatives of the CTLA4Ig fusion protein as described above may be used to regulate T cell proliferation. For example, the fragments or derivatives may be used to block T cell proliferation in graft versus host (GVH) disease which accompanies allogeneic bone marrow transplantation. The CD28-mediated T cell proliferation pathway is cyclosporine-resistant, in contrast to proliferation driven by the CD3/Ti cell receptor complex (June et al., 1987, supra). Cyclosporine is relatively ineffective as a treatment for GVH disease (Storb, *Blood* 68:119-125 (1986)). GVH disease is thought to be mediated by T lymphocytes which express CD28 antigen (Storb and Thomas, *Immunol. Rev.* 88:215-238 (1985)). Thus, the CTLA4Ig fusion protein may be useful alone, or in combination with immunosuppressants such as cyclosporine, for blocking T cell proliferation in GVH disease.

Regulation of CTLA4-positive T cell interactions with B7 positive cells, including B cells, by the methods of the invention may thus be used to treat pathological conditions such as autoimmunity, transplantation, infectious diseases and neoplasia.

The following examples are presented to illustrate the present invention and to assist one of ordinary skill in making and using the same. The examples are not intended in any way to otherwise limit the scope of the invention.

EXAMPLE 1

Preparation of B7Ig and CD28Ig Fusion Proteins

Receptor-immunoglobulin C gamma (IgCγ) fusion proteins B7Ig and CD28Ig were prepared as described by Linsley et al., in *J. Exp. Med.* 173:721-730 (1991), incorporated by reference herein. Briefly, DNA encoding amino acid sequences corresponding to the respective receptor protein (e.g. B7) was joined to DNA encoding amino acid sequences corresponding to the hinge, CH2 and CH3 regions of human IgCγ1. This was accomplished as follows.

Polymerase Chain Reaction (PCR)

For PCR, DNA fragments were amplified using primer pairs as described below for each fusion protein. PCR reactions (0.1 ml final volume) were run in Taq polymerase buffer (Stratagene, La Jolla, Calif.), containing 20 μmoles each of dNTP; 50-100 pmoles of the indicated primers; template (1 ng plasmid or cDNA synthesized from <1 μg total RNA using random hexamer primer, as described by Kawasaki in PCR Protocols, Academic Press, pp. 21-27 (1990), incorporated by reference herein); and Taq polymerase (Stratagene). Reactions were run on a thermocycler (Perkin Elmer Corp., Norwalk, Conn.) for 16-30 cycles (a typical cycle consisted of steps of 1 min at 94° C., 1-2 min at 50° C. and 1-3 min at 72° C.).

Plasmid Construction

Expression plasmids containing cDNA encoding CD28, as described by Aruffo and Seed, *Proc. Natl. Acad. Sci. USA* 84:8573 (1987)), were provided by Drs. Aruffo and Seed (Mass General Hospital, Boston, Mass.). Plasmids containing cDNA encoding CD5, as described by Aruffo, *Cell* 61:1303 (1990)), were provided by Dr. Aruffo. Plasmids containing cDNA encoding B7, as described by Freeman et al., *J. Immunol.* 143:2714 (1989)), were provided by Dr. Freeman (Dana Farber Cancer Institute, Boston, Mass.). For initial attempts at expression of soluble forms of CD28 and B7, constructs were made (OMCD28 and OMB7) as described by Linsley et al., *J. Exp. Med.,* supra, in which stop codons were introduced upstream of the transmembrane domains and the native signal peptides were replaced with the signal peptide from oncostatin M (Malik et al., Mol. Cell Biol. 9:2847 (1989)). These were made using synthetic oligonucleotides for reconstruction (OMCD28) or as primers (OMB7) for PCR. OMCD28, is a CD28 cDNA modified for more efficient expression by replacing the signal peptide with the analogous region from oncostatin M. CD28Ig and B7Ig fusion constructs were made in two parts. The 5' portions were made using OMCD28 and OMB7 as templates and the oligonucleotide, CTAGCCACT-GAAGCTTCACCATGGGTGTACTGCTCACAC (SEQ ID NO:1), (encoding the amino acid sequence corresponding to the oncostatin M signal peptide) as a forward primer, and either TGGCATGGGCTCCT-GATCAGGCTTAGAAGGTCCGGGAAA (SEQ ID NO:2), or, TTTGGGCTCCTGATCAG-GAAAATGCTCTTGCTTGGTTGT (SEQ ID NO:3) as reverse primers, respectively. Products of the PCR reactions were cleaved with restriction endonucleases (Hind III and BclI) as sites introduced in the PCR primers and gel purified.

The 3' portion of the fusion constructs corresponding to human IgCγ1 sequences was made by a coupled reverse transcriptase (from Arian myeloblastosis virus; Life Sciences Associates, Bayport, N.Y.)-PCR reaction using RNA from a myeloma cell line producing human-mouse chimetic mAb L6 (provided by Dr. P. Fell and M. Gayle, Bristol-Myers Squibb Company, Pharmaceutical Research Institute, Seattle, Wash.) as template. The oligonucleotide, AAGCAAGAGCATTTTCCT-GATCAGGAGCCCAAATCTTCTGACAAAACT-CACACATCCCCACC GTCCCCAGCACCT-GAACTCCTG (SEQ ID NO:4), was used as forward primer, and CTTCGACCAGTCTAGAAG-CATCCTCGTGCGACCGCGAGAGC (SEQ ID NO:5) as reverse primer. Reaction products were cleaved with BclI and XbaI and gel purified. Final constructs were assembled by ligating HindIII/BclI cleaved fragments containing CD28 or B7 sequences together with BclI/XbaI cleaved fragment containing IgCγ1 sequences into HindIII/XbaI cleaved CDM8. Ligation products were transformed into MC1061/p3 E. coli cells and colonies were screened for the appropriate plasmids. Sequences of the resulting constructs were confirmed by DNA sequencing.

The construct encoding B7 contained DNA encoding amino acids corresponding to amino acid residues from approximately position 1 to approximately position 215 of the extracellular domain of B7. The construct encoding CD28 contained DNA encoding amino acids corresponding to amino acid residues from approximately position 1 to approximately position 134 of the extracellular domain of CD28.

CD5Ig was constructed in identical fashion, using CATTGCACAGTCAAGCTTCCATGC-CCATGGGTTCTCTGGCCACCTTG (SEQ ID NO:6), as forward primer and ATCCACAGT-GCAGTGATCATTTGGATCCTGGCATGTGAC (SEQ ID NO:7) as reverse primer. The PCR product was restriction endonuclease digested and ligated with the IgCγ1 fragment as described above. The resulting construct (CD5Ig) encoded a mature protein having an amino acid sequence containing amino acid residues from position 1 to position 347 of the sequence corresponding to CD5, two amino acids introduced by the construction procedure (amino acids DQ), followed by DNA encoding amino acids corresponding to the IgCγ1 hinge region.

Cell Culture and Transfections

COS (monkey kidney cells) were transfected with expression plasmids expressing CD28 and B7 using a modification of the protocol of Seed and Aruffo (*Proc. Natl. Acad. Sci.* 84:3365 (1987)), incorporated by reference herein. Cells were seeded at $10^6$ per 10 cm diameter culture dish 18-24 h before transfection. Plasmid DNA was added (approximately 15 μg/dish) in a volume of 5 mls of serum-free DMEM containing 0.1 mM cloroquine and 600 μg/ml DEAE Dextran, and cells were incubated for 3-3.5 h at 37° C. Transfected cells were then briefly treated (approximately 2 min) with 10% dimethyl sulfoxide in PBS and incubated at 37° C. for 16-24 h in DMEM containing 10% FCS. At 24 h after transfection, culture medium was removed and replaced with serum-free DMEM (6 ml/dish). Incubation was continued for 3 days at 37° C., at which time the spent medium was collected and fresh serum-free medium was added. After an additional 3 days at 37° C., the spent medium was again collected and cells were discarded.

CHO cells expressing CD28, CD5 or B7 were isolated as described by Linsley et al., (1991) supra, as follows: Briefly, stable transfectants expressing CD28, CD5, or B7, were isolated following cotransfection of dihydrofolate reductase-deficient Chinese hamster ovary (dhfr− CHO) cells with a mixture of the appropriate expression plasmid and the selectable marker, pSV2dhfr (Linsley et al., *Proc. Natl. Acad.* Sci. USA 87:5031 (1990)), incorporated by reference herein. Transfectants were then grown in increasing concentrations of methotrexate to a final level of 1 μM and were maintained in DMEM supplemented with 10% fetal bovine serum (FBS), 0.2 mM proline and 1 μM methotrexate. CHO lines expressing high levels of CD28 (CD28+ CHO) or B7 (B7+ CHO) were isolated by multiple rounds of fluorescence-activated cell sorting (FACS[R]) following indirect immunostaining with mAbs 9.3 or BB-1. Amplified CHO cells negative for surface expression of CD28 or B7 (dhfr+ CHO) were also isolated by FACS[R] from CD28-transfected populations.

Immunostaining and FACS[R] Analysis

Transfected CHO or COS cells or activated T cells were analyzed by indirect immunostaining. Before staining, CHO cells were removed from their culture vessels by incubation in PBS containing 10 mM EDTA. Cells were first incubated with murine mAbs 9.3 (Hansen et al., *Immunogenetics* 10:247 (1980)) or BB-1 (Yokochi et al., *J. Immunol.* 128:823 (1981)), or with Ig fusion proteins (all at 10 μg/ml in DMEM containing 10% FCS) for 1-2 h at 4° C. Cells were then washed, and incubated for an additional 0.5-2h at 4° C. with a FITC-conjugated second step reagent (goat anti-mouse Ig serum for murine mAbs, or goat anti-human Ig Cγ serum for fusion proteins (Tago, Inc., Burlingame, Calif.)). Fluorescence was analyzed on a FACS IV[R] cell sorter (Becton Dickinson and CO., Mountain View, Calif.) equipped with a four decade logarithmic amplifier.

Purification of Ig Fusion Proteins

The first, second and third collections of spent serum-free culture media from transfected COS cells were used as sources for the purification of Ig fusion proteins. After removal of cellular debris by low speed centrifugation, medium was applied to a column (approximately 200-400 ml medium/ml packed bed volume) of immobilized protein A (Repligen Corp., Cambridge, Mass.) equilibrated with 0.05M sodium citrate, pH 8.0. After application of the medium, the column was washed with 1M potassium phosphate, pH 8, and bound protein was eluted with 0.05M sodium citrate, pH 3. Fractions were collected and immediately neutralized by addition of 1/10 volume of 2M Tris, pH 8. Fractions containing the peak of $A_{280}$ absorbing material were pooled and dialyzed against PBS before use. Extinction coefficients of 2.4 and 2.8 ml/mg for CD28Ig and B7Ig, respectively, by amino acid analysis of solutions of known absorbance. The recovery of purified CD28Ig and B7Ig binding activities were nearly quantitative as judged by FACS$^R$ analysis after indirect fluorescent staining of B7+ and CD28+ CHO cells.

EXAMPLE 2

Preparation of CTLA4Ig Fusion Protein

A soluble genetic fusion encoding CTLA4Ig between the extracellular domain of CTLA4 and an IgCγ1 domain was constructed in a manner similar to that described above for the CD28Ig construct. The extracellular domain of the CTLA4 gene was cloned by PCR using synthetic oligonucleotides corresponding to the published sequence (Dariavach et al., *Eur. Jour. Immunol.* 18:1901–1905 (1988)).

Because a signal peptide for CTLA4 was not identified in the CTLA4 gene, the N-terminus of the predicted sequence of CTLA4 was fused to the signal peptide of oncostatin M (Malik et al., *Mol. and Cell. Biol.* 9:2847 (1989)) in two steps using overlapping oligonucleotides. For the first step, the oligonucleotide, CTCAGTCTGGTCCTTGCACTCCTG TTTCCAAGCATGGCGAGCATGGCAATG- CACGTGGCCCAGCC (SEQ ID NO:8) (which encoded the C terminal 15 amino acids from the oncostatin M signal peptide fused to the N terminal 7 amino acids of CTLA4) was used as forward primer, and TTTGGGCTCCTGATCAGAATCTGG- GCACGGTTG (SEQ ID NO:9) (encoding amino acid residues 119-125 of the amino acid sequence encoding CTLA4 receptor and containing a Bcl I restriction enzyme site) as reverse primer. The template for this step was cDNA synthesized from 1 μg of total RNA from H38 cells (an HTLV II infected T cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGCCACTGAAGCTT- CACCAATGGGTGTACTGCTCACACAGAG- GACGCTGCTCAGTCTGGT CCTTGCACTC (SEQ ID NO:10) and the same reverse primer. The product of the PCR reaction was digested with Hind III and Bcl I and ligated together with a Bcl 1/Xba I cleaved cDNA fragment encoding the amino acid sequences corresponding to the hinge, CH2 and CH3 regions of IgCγ1 into the Hind III/Xba I cleaved expression vector, CDM8 or Hind III/Xba I cleaved expression vector πLN (provided by Dr. Aruffo).

A map of the resulting CTLA4Ig fusion construct is shown in FIG. 1. Sequences displayed in this figure show the junctions between CTLA4 (upper case letters, unshaded regions) and the signal peptide, SP, of oncostatin M (dark shaded regions), and the hinge, H, of IgCγ1 (stippled regions). The amino acid in parentheses was introduced during construction. Asterisks (*) indicate cysteine to serine mutations introduced in the IgCγ hinge region. The immunoglobulin superfamily V-like domain present in CTLA4 is indicated, as are the CH2 and CH3 domains of IgCγ1.

Expression plasmids, CDM8, containing CTLA4Ig were then transfected into COS cells using DEAE/dextran transfection by modification (Linsley et al., 1991, supra) of the protocol described by Seed and Aruffo, 1987, supra.

Expression plasmid constructs (πLN or CDM8) containing cDNA encoding the amino acid sequence of CTLA4Ig, was transfected by lipofection using standard procedures into dhfr− CHO lines to obtain novel cell lines stably expressing CTLA4Ig.

DNA encoding the amino acid sequence corresponding to CTLA4Ig has been deposited with the ATCC under the Budapest Treaty on May 31, 1991, and has been accorded ATCC accession number 68629.

A preferred stable transfectant, expressing CTLA-4Ig, designated Chinese Hamster Ovary Cell Line, CTLA4Ig-24, was made by screening B7 positive CHO cell lines for B7 binding activity in the medium using immunostaining. Transfectants were maintained in DMEM supplemented with 10% fetal bovine serum (FBS), 0.2 mM proline and 1 μM methotrexate.

The CTLA4Ig-24 CHO cell line has been deposited with the ATCC under the Budapest Treaty on May 31, 1991 and has been accorded accession number ATCC 10762.

Figure 2:
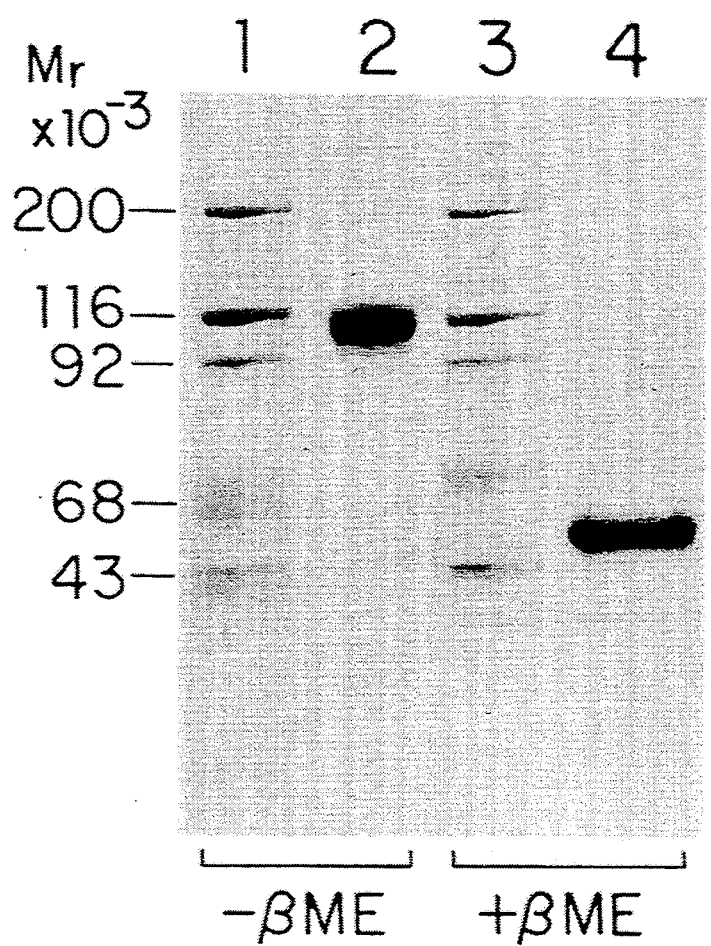
FIG. 2 is a photograph of a gel obtained from SDS-PAGE chromatographic purification of CTLA4Ig as described in Example 2, infra.

CTLA4Ig was purified by protein A chromatography from serum-free conditioned supernatants (FIG. 2). Concentrations of CTLA4Ig were determined assuming an extinction coefficient at 280 nm of 1.6 (experimentally determined by amino acid analysis of a solution of known absorbance). Molecular weight standards (lanes 1 and 3, FIG. 2) and samples (1 μg) of CTLA4Ig (lanes 2 and 4) were subjected to SDS-PAGE (4–12% acrylamide gradient) under nonreducing conditions (−BME, lanes 1 and 2) or reducing conditions (+BME, lanes 3 and 4) Proteins were visualized by staining with Coomassie Brilliant Blue.

Under non-reducing conditions, CTLA4Ig migrated as a $M_r$ approximately 100,000 species, and under reducing conditions, as a $M_r$ approximately 50,000 species (FIG. 2). Because the IgC γ hinge disulfides were eliminated during construction, CTLA4Ig, like CD28Ig, is a dimer presumably joined through a native disulfide linkage.

EXAMPLE 3

CTLA4 Receptor

To reconstruct DNA encoding the amino acid sequence corresponding to the full length human CTLA4 gene, cDNA encoding amino acids corresponding to a fragment of the transmembrane and cytoplasmic domains of CTLA4 was cloned by PCR and then joined with cDNA encoding amino acids corresponding to a fragment from CTLA4Ig that corresponded to the oncostatin M signal peptide fused to the N-terminus of CTLA4. Procedures for PCR, and cell culture and transfections were as described above in Example 1 using COS cells and DEAE-dextran transfection.

Because the expression of CTLA4 receptor protein in human lymphoid cells has not been previously reported, it was necessary to locate a source of CTLA4 mRNA. PCR cDNA reverse transcribed from the total cellular RNA of H38 cells, as noted above, was used for cloning by PCR. For this purpose, the oligonucleotide, GCAATGCACGTGGCCCAGCCTGCTGTG- GTAGTG (SEQ ID NO:! 1), (encoding the first 11 amino acids in the predicted coding sequence) was used as a forward primer, and TGATGTAACATGT- CTAGATCAATTGATG- GGAATAAAATAAGGCTG (SEQ ID NO:12) (homologous to the last 8 amino acids in CTLA4 and containing a Xba I site) as reverse primer. The template again was a cDNA synthesized from 1 μg RNA from H38 cells. Products of the PCR reaction were cleaved with the restriction endonucleases Nco I and Xba I and the resulting 316 bp product was gel purified. A 340 bp Hind III/Nco I fragment from the CTLAIg fusion described above was also gel-purified, and both restriction fragments were ligated into Hind III/Xba I cleaved CDM8 to form OMCTA.

The resulting construct corresponded to full length CTLA4 (SEQ ID NOs: 13 and 14) and the oncostatin M signal peptide. The construct is shown in FIG. 3 and was designated OMCTLA4. The sequence for CTLA4 shown in FIG. 3 differs from the predicted human CTLA4 DNA sequence (Dariavach et al., supra) by a base change such that the previously reported alanine at amino acid position 111 of the amino acid sequence shown, encodes a threonine. This threonine is part of a newly identified N-linked glycosylation site that may be important for successful expression of the fusion protein.

Ligation products were transformed into MC1061/p3 E. coli cells and colonies were screened for the appropriate plasmids. Sequences of the resulting constructs were confirmed by DNA sequence analysis.

EXAMPLE 4

Characterization of CTLA4Ig

To characterize the CTLA4Ig constructs, several isolates, CD28Ig, B7Ig, and CD5Ig, were prepared as described above and were transfected into COS cells as described in Examples 2 and 3, and were tested by FACS$^R$ analysis for binding of B7Ig. In addition to the above-mentioned constructs, CDM8 plasmids containing cDNAs encoding CD7 as described by Aruffo and Seed, (EMBO Jour. 6:3313-3316 (1987)), incorporated by reference herein, were also used.

mAbs. Murine monoclonal antibodies (mAbs) 9.3 (anti-CD28) and G19-4 (anti-CD3), G3-7 (anti-CD7), BB-1 (anti-B7 antigen) and rat mAb 187.1 (anti-mouse K chain) have been described previously (Ledbetter et al., Proc. Natl. Acad. Sci. 84:1384-1388 (1987); Ledbetter et al., Blood 75:1531 (1990); Yokochi et al., supra) and were purified from ascites before use. The hybridoma producing mAb OKT8 was obtained from the ATCC, Rockville, Md., and the mAb was also purified from ascites before use. mAb 4G9 (anti-CD19) was provided by Dr. E. Engleman, Stanford University, Palo Alto, Calif.). Purified human-mouse chimeric mAb L6 (having human Cγ1 Fc portion) was a gift of Dr. P. Fell and M. Gayle (Bristol-Myers Squibb Pharmaceutical Research Institute, Seattle, Wash.).

Immunostaining and FACS$^R$ Analysis

Prior to staining, COS or CHO cells were removed from their culture vessels by incubation in PBS containing 10 mM EDTA. Cells were first incubated with mAbs or Ig fusion proteins at 10 μg/ml in DMEM containing 10% FBS for 1-2 hr at 4° C. Cells were then washed, and incubated for an additional 0.5-2 hrs at 4° C. with FITC-conjugated goat anti-mouse immunoglobulin or with FITC-conjugated goat anti-human Ig C γ serum (both from Tago, Burlingame, Calif.). When binding of both mAbs and Ig fusion proteins were measured in the same experiment, FITC-conjugated anti-mouse and anti-human second step reagents were mixed together before use. Fluorescence on a total of 10,000. cells was then analyzed by FACS$^R$.

Peripheral Blood Lymphocyte Separation and Stimulation

Peripheral blood lymphocytes (PBLs) were isolated by centrifugation through Lymphocyte Separation Medium (Litton Bionetics, Kensington, Md.). Alloreactive T cells were isolated by stimulation of PBL in a primary mixed lymphocyte reaction (MLR). PBL were cultured at $10^6$/ml irradiated (5000 rad) T51 LCL. EBV-transformed lymphoblastoid cell lines (LCL), PM (Bristol-Myers Squibb Co.) and T51 (Bristol-Myers Squibb Co.) were maintained in RPMI supplemented with 10% FBS. After 6 days, alloreactive "blasts" cells were cryopreserved. Secondary MLR were conducted by culturing thawed alloreactive blasts together with fresh irradiated T51 LCL in the presence and absence of mAbs and Ig fusion proteins. Cells were cultured in 96 well flat bottom plates ($4\times10^4$ alloreactive blasts and $1\times10^4$ irradiated T51 LCL cells/well, in a volume of 0.2 ml) in RPMI containing 10% FBS. Cellular proliferation of quadruplicate cultures was measured by uptake of [$^3$H]-thymidine during the last 6 hours of a 2-3 day culture.

PHA-activated T cells were prepared by culturing PBLs with 1 μg/ml PHA (Wellcome, Charlotte, N.C.) for five days, and one day in medium lacking PHA. Viable cells were collected by sedimentation through Lymphocyte Separation Medium before use. Cells were stimulated with mAbs or transfected CHO cells for 4-6 hr at 37° C., collected by centrifugation and used to prepare RNA.

CD4+ T cells were isolated from PBLs by separating PBLs from healthy donors into T and non-T cells using sheep erythrocyte rosetting technique and further separating T cells by panning into CD4+ cells as described by Damle et al., J. Immunol. 139:1501 (1987), incorporated by reference herein. B cells were also purified from peripheral blood by panning as described by Wysocki and Sato, Proc. Natl. Acad. Sci. 75:2844 (1978), incorporated by reference herein, using anti-CD19 mAb 4G9. To measure T$_h$-induced Ig production, $10^6$ CD4+ T cells were mixed with $10^6$ CD19+ B cells in 1 ml of RPMI containing 10% FBS. Following culture for 6 days at 37° C., production of human IgM was measured in the culture supernatants-using solid phase ELISA as described by Volkman et al., Proc. Natl. Acad. Sci. USA 78:2528 (1981), incorporated by reference herein. Briefly, 96-well flat bottom microtiter ELISA plates (Corning, DO Corning, N.Y.) were coated with 200 μl/well of sodium carbonate buffer (pH 9.6) containing 10 μg/ml of affinity-purified goat anti-human IgG or IgM antibody (Tago, Burlingame, Calif.), incubated overnight at 4° C., and then washed with PBS and wells were further blocked with 2% BSA in PBS (BSA-PBS). Samples to be assayed were added at appropriate dilution to these wells and incubated with 200 μl/well of 1:1000 dilution of horseradish peroxidase (HRP)-conjugated F(ab')$_2$ fraction of affinity-purified goat anti-human IgG or IgM antibody (Tago). The plates were then washed, and 100 μl/well of o-phenylenediamine (Sigma Chemical Co., St. Louis, Mo.) solution (0.6 mg/ml in citrate-phosphate buffer with pH 5.5 and 0.045% hydrogen peroxide). Color development was stopped with 2N sulfuric acid. Absorbance at 490 nm was measured with an automated ELISA plate reader. Test and control samples were run in triplicate and the values of absorbance were compared to those obtained with known IgG or IgM standards run simultaneously with the supernatant samples to generate the standard curve using which the concentrations of Ig in the culture supernatant were quantitated. Data are expressed as ng/ml of Ig±SEM of either triplicate or quadruplicate cultures.

Immunoprecipitation Analysis and SDS PAGE

Cells were surface-labeled with $^{125}I$ and subjected to immunoprecipitation analysis. Briefly, PHA-activated T cells were surface-labeled with $^{125}I$ using lactoperoxidase and $H_2O_2$ as described by Vitetta et al., *J. Exp. Med.* 134:242 (1971), incorporated by reference herein. SDS-PAGE chromatography was performed on linear acrylamide gradients gels with stacking gels of 5% acrylamide. Gels were stained with Coomassie Blue, destained, and photographed or dried and exposed to X ray film (Kodak XAR-5).

Binding Assays

B7Ig was labeled with $^{125}I$ to a specific activity of approximately $2 \times 10^6$ cpm/pmole. Ninety-six well plastic dishes were coated for 16-24 hrs with a solution containing CTLA4Ig (0.5 μg in a volume of 0.05 ml of 10 mM Tris, pH 8). Wells were blocked with binding buffer (DMEM containing 50 mM BES (Sigma Chemical Co.), pH 6.8, 0.1% BAS, and 10% FCS) before addition of a solution (0.09 ml) containing $^{125}I$ B7Ig (approximately $5 \times 10^5$ cpm) in the presence or absence of competitor. Following incubation for 2-3 hrs at 23° C., wells were washed once with binding buffer, and four times with PBS. Bound radioactivity was then solubilized by addition of 0.5N NaOH, and quantified by gamma counting.

Binding to B7Ig

Figure 4:
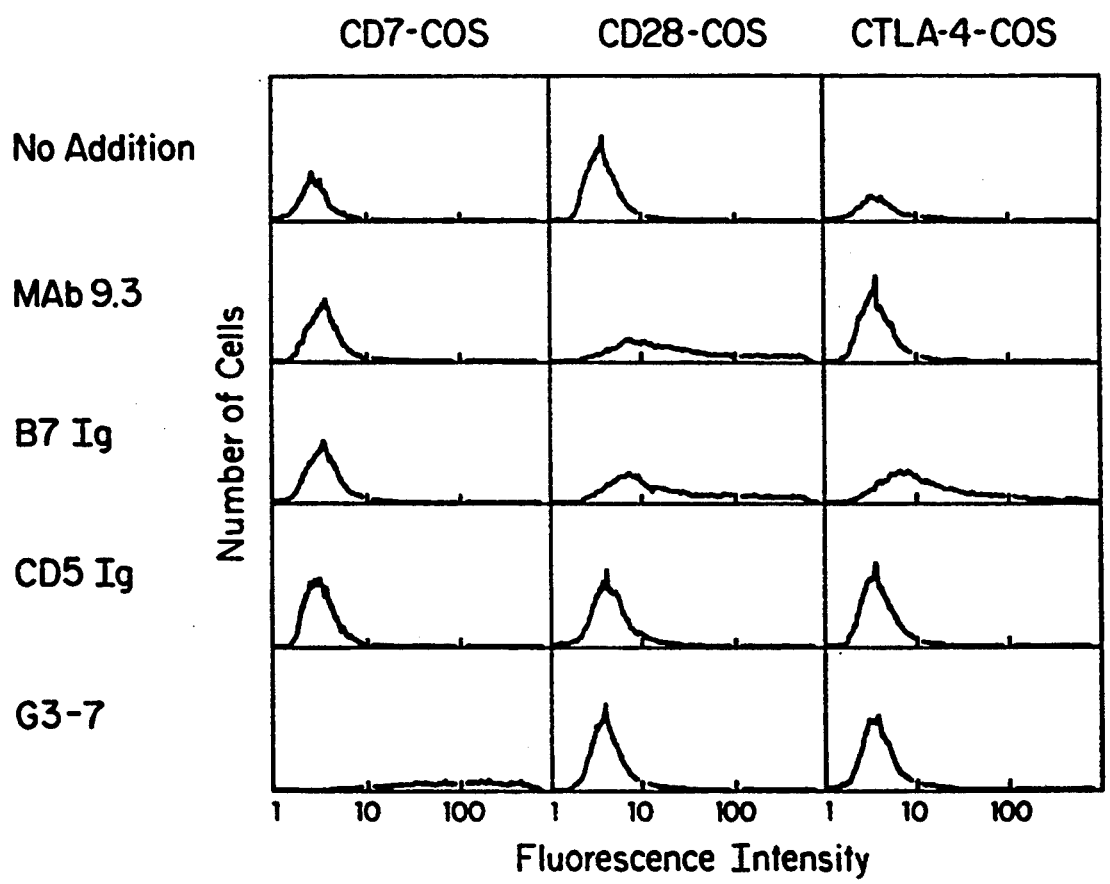
FIG. 4 depicts the results of FACS$^R$ analysis of binding of the B7Ig fusion protein to CD28- and CTLA4-transfected COS cells as described in Example 4, infra.

The functional activity of the OMCTLA4 construct encoding the complete human CTLA4 DNA gene, is shown in the experiment shown in FIG. 4. COS cells were transfected with expression plasmids CD7, OMCD28 and OMCTLA4 as described above. Forty-eight hours following transfection, cells were collected and incubated with medium only (no addition) or with mAbs 9.3, B7Ig, CD5Ig or G3-7. Cells were then washed and binding was detected by a mixture of FITC-conjugated goat anti-mouse Ig and FITC-conjugated goat anti-human Ig second step reagents. Transfected cells were tested for expression of the appropriate cell surface markers by indirect immunostaining and fluorescence was measured using $FACS^R$ analysis as described above.

As shown in FIG. 4, mAb 9.3 bound to CD28-transfected COS cells, but not to CTLA4-transfected cells. In contrast, the B7Ig fusion protein (but not control CD5Ig fusion protein) bound to both CD28- and CTLA4-transfected cells. CD7-transfected COS cells bound neither mAb 9.3 nor either of the fusion proteins. This indicates that CD28 and CTLA4 both bind the B cell activation antigen, B7. Furthermore, mAb 9.3 did not detectably bind CTLA4.

Binding of CTLA4Ig on B7 Positive CHO cells

Figure 5:
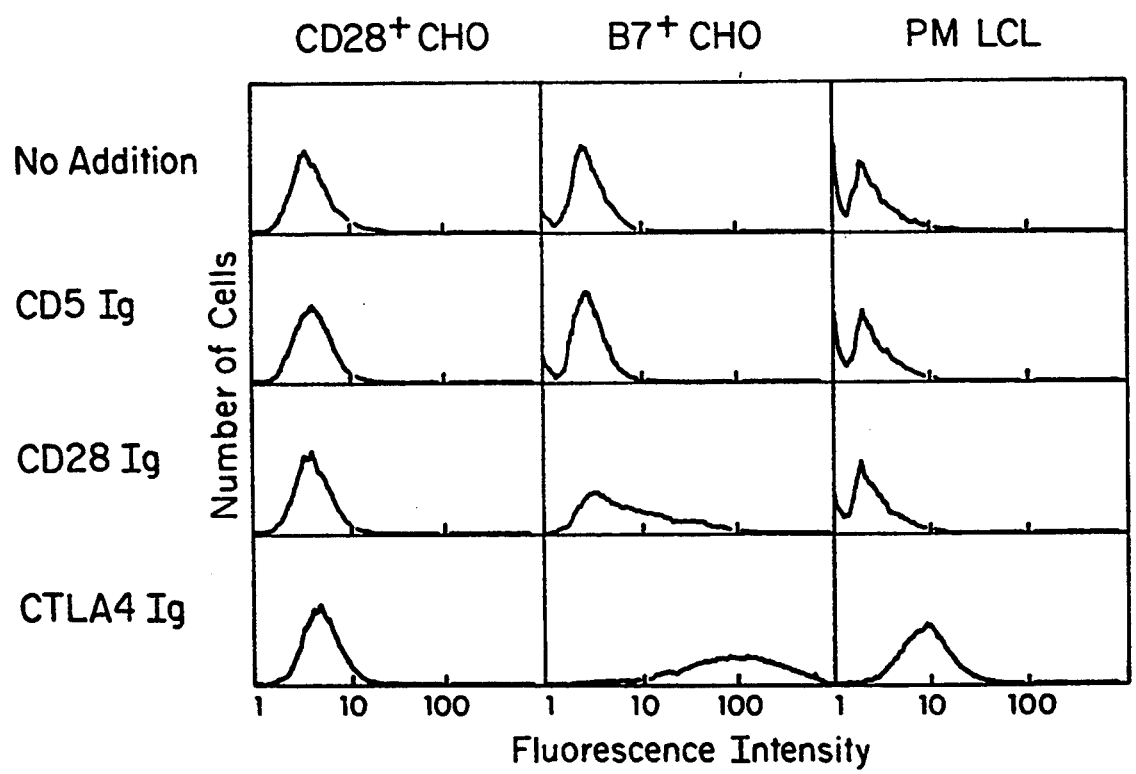
FIG. 5 depicts the results of FACS$^R$ analysis of binding of purified CTLA4Ig on B7 antigen-positive (B7+) CHO cells and on a lymphoblastoid cell line (PM LCL) as described in Example 4, infra.

To further characterize the binding of CTLA4Ig and B7, the binding activity of purified CTLA4Ig on B7+ CHO cells and on a lymphoblastoid cell line (PM LCL) was measured in the experiment shown in FIG. 5. Amplified transfected CHO cell lines and PM LCLs were incubated with medium only (no addition) or an equivalent concentration of human IgCγ1-containing proteins (10 μg/ml) of CD5Ig, CD28Ig or CTLA4Ig. Binding was detected by $FACS^R$ following addition of FITC-conjugated goat anti-human Ig second step reagents. A total of 10,000 stained cells were analyzed by $FACS^R$.

As shown in FIG. 5, CD28Ig bound to B7+ CHO cells but not to PM LCL, a cell line which expresses relatively low levels of the B7 antigen (Linsley et al., supra, 1990). CTLA4Ig bound more strongly to both cell lines than did CD28Ig, suggesting that it bound with higher affinity. Neither CD28Ig nor CTLA4Ig bound to CD28+ CHO cells.

Affinity of Binding of CTLA4Ig and B7Ig

The apparent affinity of interaction between CTLA4Ig and B7Ig was then measured using a solid phase competition binding assay. Ninety-six well plastic dishes were coated with CTLA4Ig as described above. B7Ig was radiolabeled with $^{125}I$ ($5 \times 10^5$ cpm, $2 \times 10^6$ cpm/pmole), and added to a concentration of 4 nM in the presence of the indicated concentrations (see FIG. 6) of unlabeled chimeric mAb L6, mAb 9.3, mAb BB-1 or B7Ig. Plate-bound radioactivity was determined and expressed as a percentage of radioactivity bound to wells treated without competitor (28,300 cpm). Each point represents the mean of duplicate determinations; replicates generally varied from the mean by <20%. Concentrations were calculated based on a $M_r$ of 75,000 per binding site for mAbs and 51,000 per binding site for B7Ig.

Figure 6:
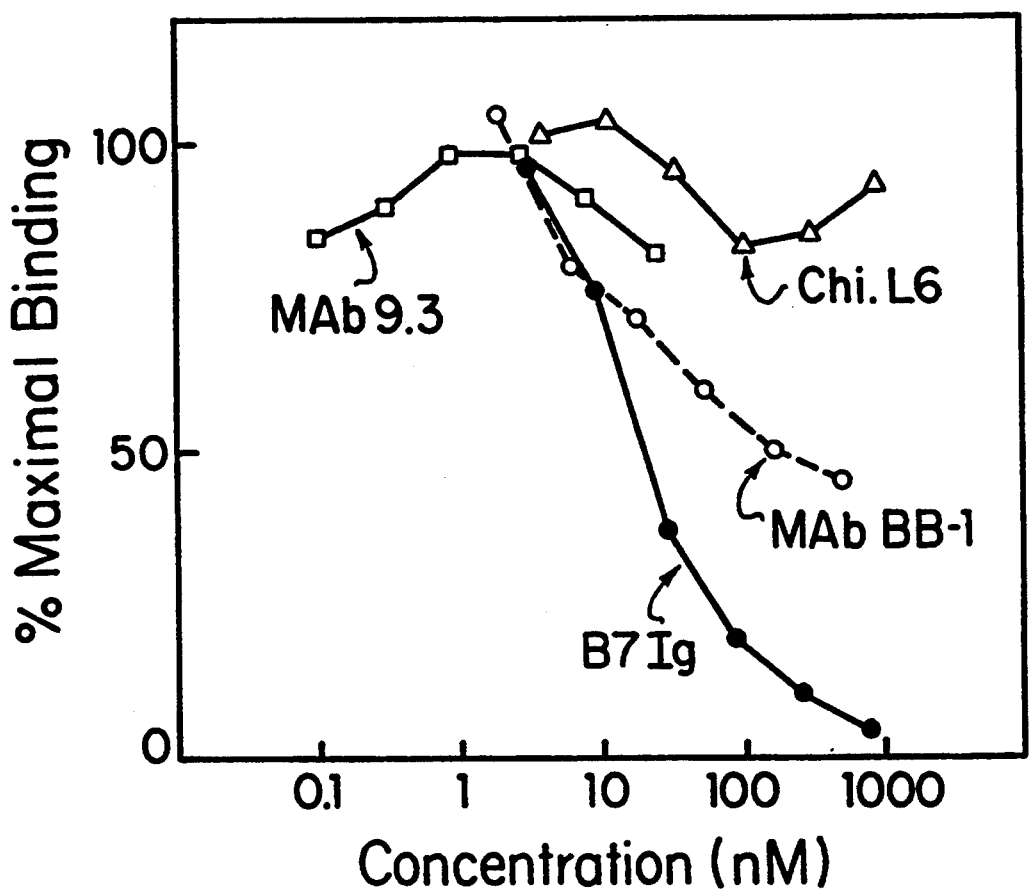
FIG. 6 is a graph illustrating competition binding analysis of $^{125}$I-labeled B7Ig to immobilized CTLA4Ig as described in Example 4, infra.

As shown in FIG. 6, only mAb BB-1 and unlabeled B7Ig competed significantly for $^{125}I$-B7Ig binding (half maximal effects at approximately 22 nM and approximately 175 nM, respectively). Neither chimeric mAb L6, nor mAb 9.3 competed effectively at the concentrations tested. In other experiments, the concentrations of mAb 9.3 used were sufficient to inhibit binding of $^{125}I$-B7Ig to immobilized CD28Ig or to cell surface expressed CD28 by >90%.

Figure 7:
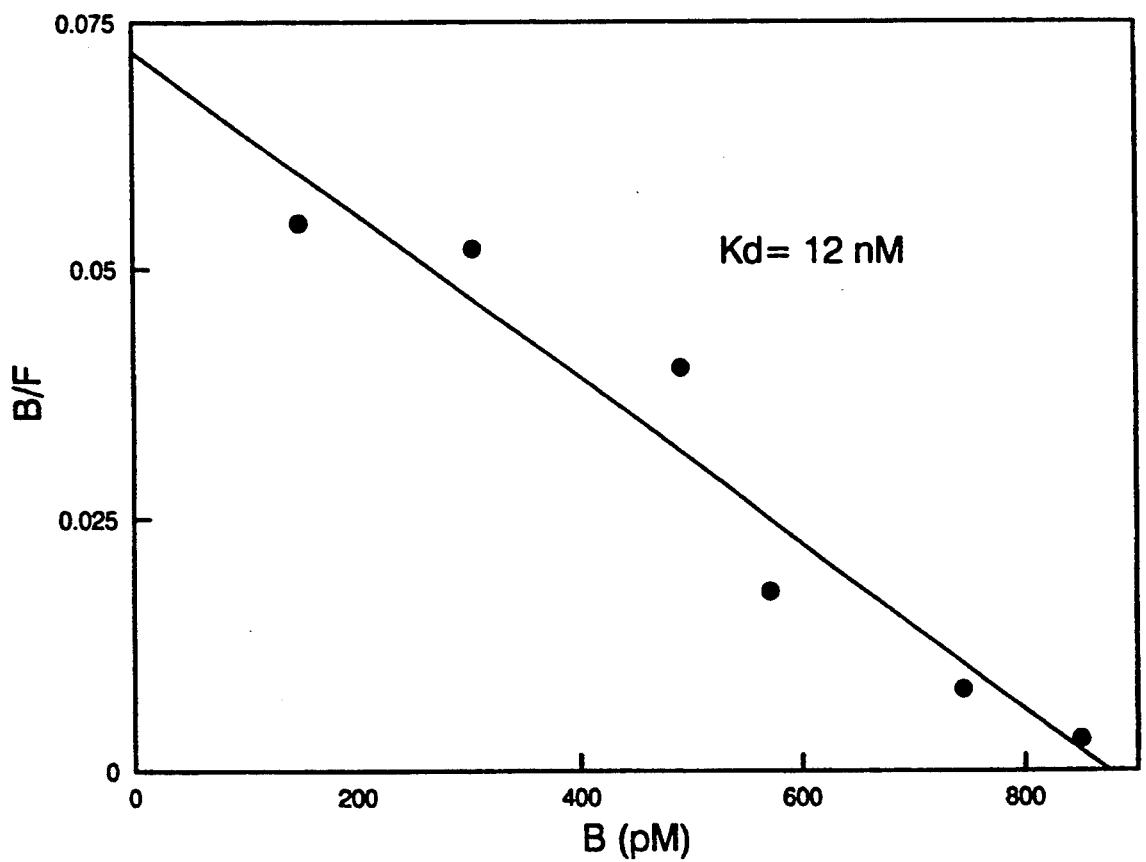
FIG. 7 is a graph showing the results of Scatchard analysis of $^{125}$I-labeled B7Ig binding to immobilized CTLA4Ig as described in Example 4, infra.

When the competition data from FIG. 6 were plotted in a Scatchard representation, a dissociation constant, $K_d$, of approximately 12 nM was calculated for binding of $^{125}I$-B7 to immobilized CTLA4Ig (FIG. 7). This value is approximately 20 fold lower than the previously determined $K_d$ of binding between $^{125}I$-B7Ig and CD28 (approximately 200 nM) (Linsley et al, (1991), supra) indicating that CTLA4 is a higher affinity receptor for the B7 antigen than CD2S receptor.

Figure 8:
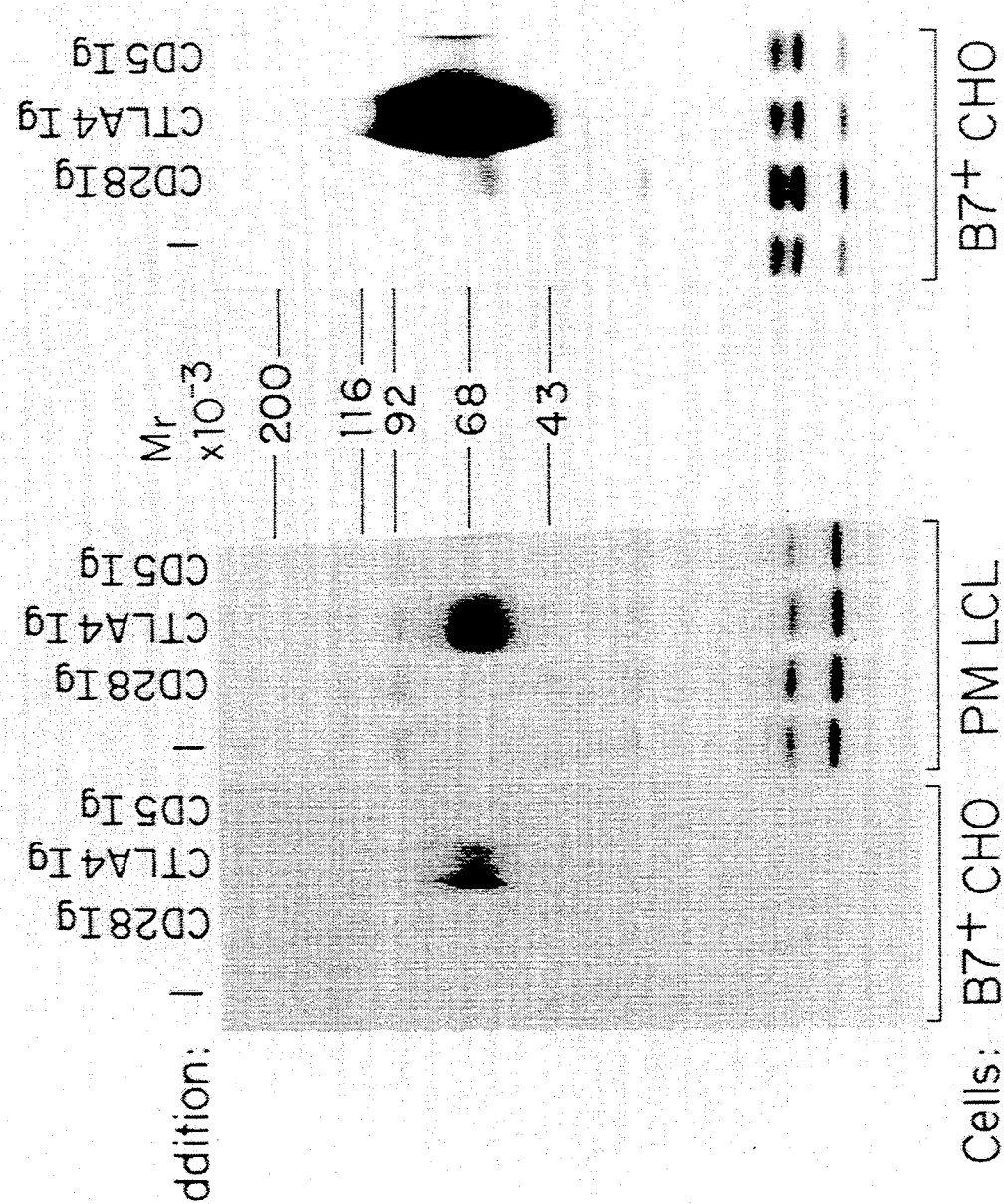
FIG. 8 is a photograph of a gel from SDS-PAGE chromatography of immunoprecipitation analysis of B7 positive CHO cells and PM LCL cells surface-labeled with $^{125}$I as described in Example 4, infra.

To identify the molecule(s) on lymphoblastoid cells which bound CTLA4Ig (FIG. 7), $^{125}I$-surface labeled cells were subjected to immunoprecipitation analysis (FIG. 8). B+ CHO and PM LCL cells were surface-labeled with $^{125}I$, and extracted with a non-ionic detergent solution as described above. Aliquots of extracts containing approximately $1.5 \times 10^7$ cpm in a volume of 0.1 ml were subjected to immunoprecipitation analysis as described above with no addition, or 2 μg each of CD28Ig, CTLA4Ig or CD5Ig. Washed immunoprecipitates were then analyzed by SDS-PAGE (10-20% acrylamide gradient) under reducing conditions. The gel was then dried and subjected to autoradiography. The left panel of FIG. 8 shows an autoradiogram obtained after a 1 day exposure. The right panel of FIG. 8 shows an autoradiogram of the same gel after a 10 day exposure. The autoradiogram in the center panel of FIG. 8 was also exposed for 10 days. Positions of molecular weight standard are also indicated in this figure.

As shown by FIG. 8, a diffusely migrating ($M_r$ approximately 50,000-75,000; center at approximately 60,000) radiolabeled protein was immunoprecipitated by CTLA4Ig, but not by CD28Ig or CD5Ig. This molecule co-migrated with B7 immunoprecipitated from B7+ CHO cells by CTLA4Ig, and much more weakly, by CD28Ig. These findings indicate that CTLA4Ig binds a single protein on lymphoblastoid cells which is similar in size to the B7 antigen.

Inhibition of Immune Responses In Vitro by CTLA4Ig

Inhibition of Proliferation

Previous studies have shown that the anti-CD28 mAb, 9.3, and the anti-B7 mAb, BB-1, inhibit proliferation of alloantigen specific $T_h$ cells, as well as immunoglobulin secretion by alloantigen-presenting B Cells (Damle, et al., Proc. Natl. Acad. Sci. 78:5096 (1981); Lesslauer et al., Eur. J. Immunol. 16:1289 (1986)). Because CTLA4 is a high affinity receptor for the B7 antigen as demonstrated herein, soluble CTLA4Ig was tested for its ability to inhibit these responses. The effects of CTLA4Ig on T cell proliferation were examined in the experiment shown in FIG. 9.

Figure 9:
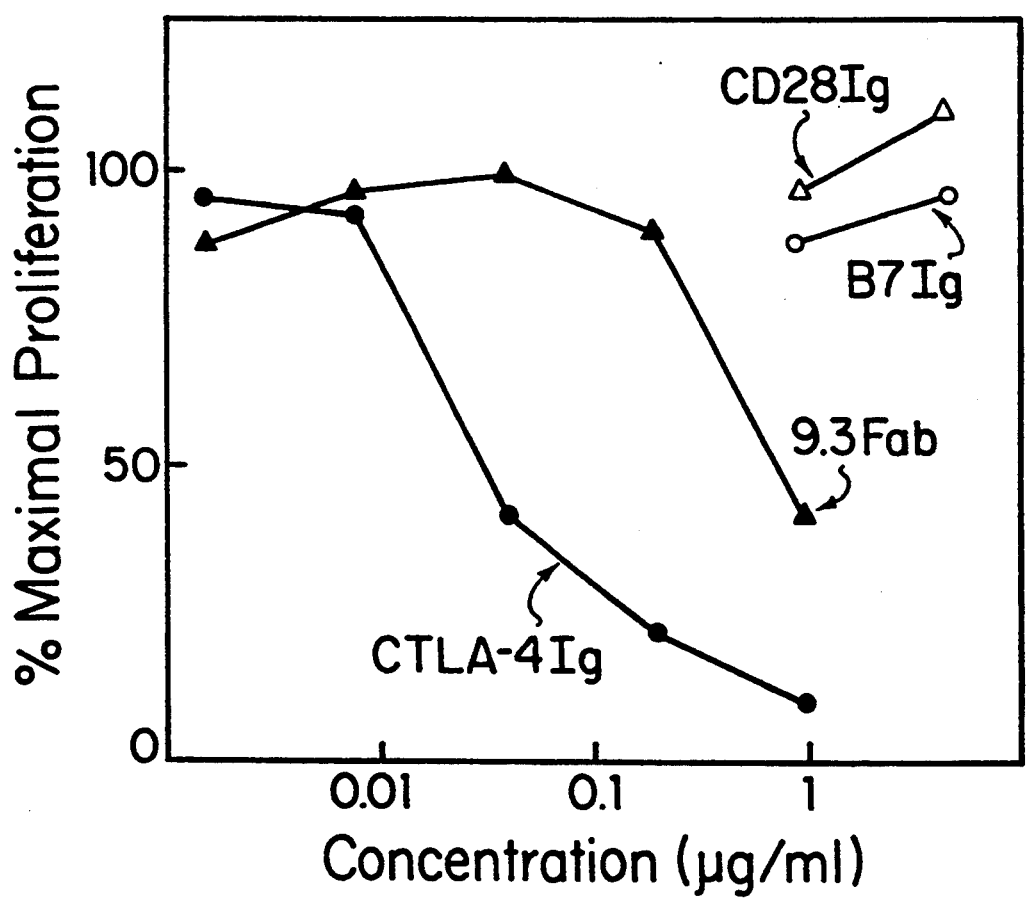
FIG. 9 is a graph depicting the effects on proliferation of T cells of CTLA4Ig as measured by [$^3$H]-thymidine incorporation as described in Example 4, infra.

Primary mixed lymphocyte reaction (MLR) blasts were stimulated with irradiated T51 lymphoblastoid cells (LC) in the absence or presence of concentrations of murine mAb Fab fragments, or B7Ig, CD28Ig or CTLA4Ig immunoglobulin Cγ fusion proteins. Cellular proliferation was measured by [$^3$H]-thymidine incorporation after 4 days and is expressed as the percentage of incorporation by untreated cultures (21,000 cpm). FIG. 9 shows the means of quadruplicate determinations (SEM <10%).

As shown in FIG. 9, CTLA4Ig inhibited the MLR reaction in a dose-dependant fashion by a maximum of >90% with a ½ maximal response at approximately 30 ng/ml (approximately 0.8 nM). The Fab fragment of mAb 9.3, which previously was shown to be a more potent inhibitor of MLR than whole mAb 9.3 (Damle et al., J. Immunol. 140:1753-1761 (1988)), also inhibited the MLR, but at higher concentrations (approximately 800 ng/ml or approximately 30 nM for ½ maximal response). B7Ig and CD28Ig did not significantly inhibit the MLR even at higher concentrations. In another experiment, addition of B7Ig together with CTLA4Ig partially overcame the inhibition of MLR by CTLA-4Ig, indicating that the inhibition was specifically due to interactions with B7 antigen.

Inhibition of Immunoglobulin Secretion

Figure 10:
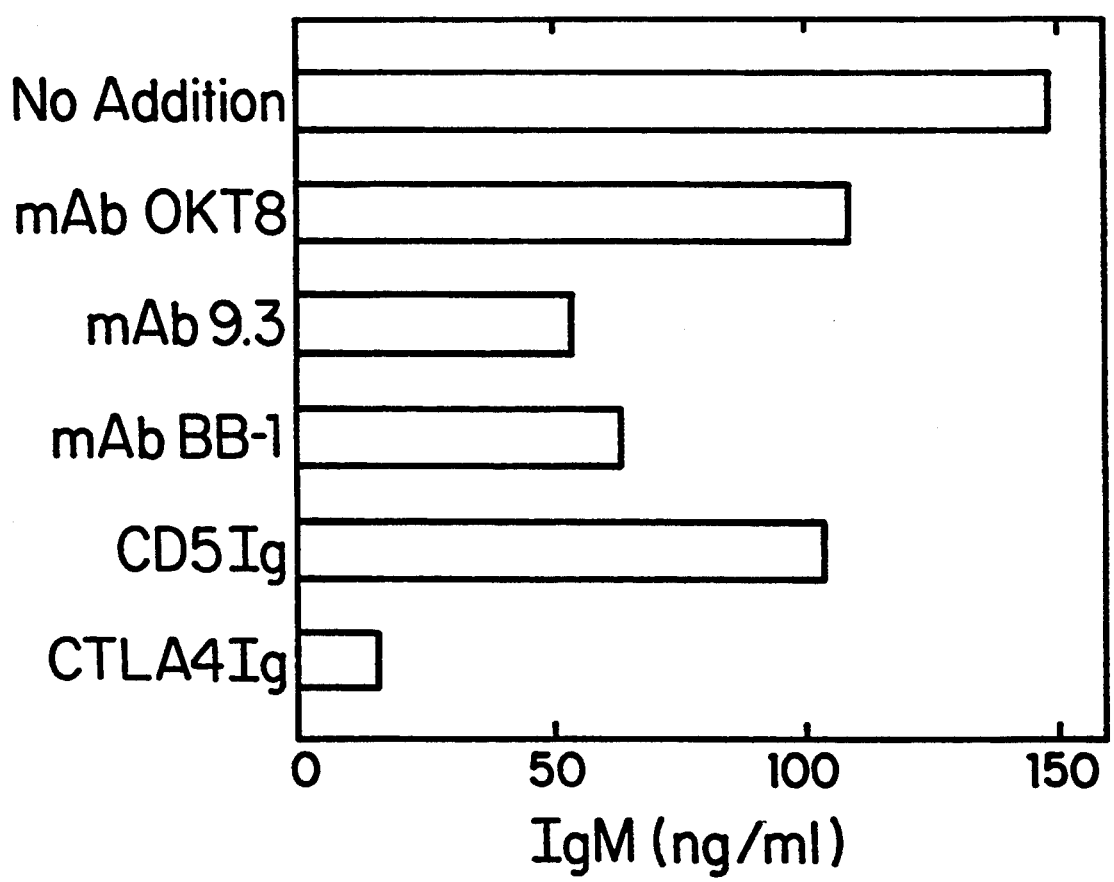
FIG. 10 is a bar graph illustrating the effects of CTLA4Ig on helper T cell ($T_h$)-induced immunoglobulin secretion by human B cells as determined by enzyme immunoassay (ELISA) as described in Example 4, infra.

The effects of CTLA4Ig on helper T cell ($T_h$)-induced immunoglobulin secretion were also examined (FIG. 10). CD4+ T cells were mixed with allogeneic CD19+ B cells in the presence or absence of the indicated immunoglobulin molecules as described above. Murine mAbs OKT8, 9.3 and BB-1 were added at 20 μg/ml, and Ig fusion proteins at 10 μg/ml. After 6 days of culture, concentrations of human IgM (SEM <5%) in culture supernatants were determined by enzyme immunoassay (ELISA) as described above. IgM production by B cells cultured in the absence of CD4+ T cells was 11 ng/ml.

As shown in FIG. 10, CD4+ T cells stimulated IgM production by allogenic CD19+ B Cells (in the absence of CD4+ T cells, IgM levels were reduced by 93%). mAbs 9.3 and BB-1 significantly inhibited $T_h$-induced IgM production (63% and 65% inhibition, respectively). CTLA4Ig was even more effective as an inhibitor (89% inhibition) than were these mAbs. Inhibition by control Ig molecules, mAb OKT8 and CD5Ig, was much less (<30%. inhibition). None of these molecules significantly inhibited Ig production measured in the presence of Staphylococcat aureus enterotoxin B. Similar results were obtained with CD4+ T cells and B cells derived from other donors. These results indicate that the inhibition by CTLA4Ig is specific.

The above data also demonstrate that the CTLA4 and CD28 receptors are functionally as well as structurally related. Like CD28, CTLA4 is also a receptor for the B cell activation antigen, B7. CTLA4Ig bound $^{125}$I-B7 with an affinity constant, $K_d$, of approximately 12 nM, a value some 20 fold higher than the affinity between CD28 and B7Ig (approximately 200 nM). Thus, CTLA4 and CD28 may be thought of as high and low affinity receptors, respectively, for the same ligand, the B7 antigen.

The apparent affinity between CD28 and B7 is similar to the affinity reported for binding of soluble alloantigen to the T cell receptor of a murine T cell hybridoma (approximately 100 nM; Schnek et al., Cell 56:47 (1989)), and is higher affinity than interactions between CD2 and LFA3 (Recny et al., J. Biol. Chem. 265:8542 (1990)), or CD4 and MHC class II molecules (Clayton et al., Nature 339:548 (1989)). The apparent affinity constant, $K_d$, between CTLA4 and B7 is even greater, and compares favorably with higher affinity mAbs ($K_d$ 2-10,000 nM; Atzari et al., Ann. Rev. Immuno. 6:555 (1988)). The $K_d$ between CTLA4 and B7 is similar to or greater than $K_d$ values of integrin receptors and their ligands (10-2000 nM; Hautanen et al., J. Biol. Chem. 264:1437-1442 (1989); Di Minno et al., Blood 61:140-148 (1983); Thiagarajan and Kelley, J. Biol. Chem. 263:035-3038 (1988)). The affinity of interaction between CTLA4 and B7 is thus among the highest yet reported for lymphoid adhesion systems.

These results demonstrate the first expression of a functional protein product of CTLA4 transcripts. CTLA4Ig, a fusion construct containing the extracellular domain of CTLA4 fused to an IgCγ1 domain, forms a disulfide-linked dimer of $M_r$ approximately 50,000 subunits (FIG. 1). Because no interchain disulfides would be predicted to form in the Ig portion of this fusion, it seems likely that cysteines from CTLA4 are involved in disulfide bond formation. The analogous CD28Ig fusion protein (Linsley et al, supra, 1991) also contains interchain disulfide linkage(s). These results suggest that CTLA4 receptor, like CD28 (Hansen et al., Immunogenetics 10:247-260 (1980)), exists on the T cell surface as a disulfide linked homodimer. Although CD28 and CTLA4 are highly homologous proteins, they are immunologically distinct, because the anti-CD28 mAb, 9.3, does not recognize CTLA4 (FIGS. 4 and 5).

It is not known whether CTLA4 can activate T cells by a signalling pathway analogous to CD28. The cytoplasmic domains of murine and human CTLA4 are identical (Dariavach et al., supra 1988), suggesting that this region has important functional properties. The cytoplasmic domains of CD28 and CTLA4 also share homology, although it is unclear if this is sufficient to impart similar signaling properties to the two molecules.

CTLA4Ig is a potent inhibitor of in vitro lymphocyte functions requiring T cell and B cell collaboration (FIGS. 9 and 10). These findings, together with previous studies, indicate the fundamental importance of interactions between B7 antigen and its counter-receptors, CD28 and/or CTLA4, in regulating both T and B lymphocyte responses. CTLA4Ig should be a useful reagent for future investigations on the role of these interactions during immune responses. CTLA4Ig is a more potent inhibitor of in vitro lymphocyte responses than either mAb BB-1 or mAb 9.3 (FIGS. 9 and 10). The greater potency of CTLA4Ig over mAb BB-1 is most likely due to the difference in affinities for B7 between these molecules (FIG. 6). CTLA4Ig is also more potent than mAb 9.3, probably because, unlike the mAb, it does not also have direct stimulatory effects on T cell proliferation (June et al., *Immunology Today* 11:211 (1989)) to counteract its inhibitory effects. The immunosuppressive effects of CTLA4Ig in vitro suggest that future investigations are warranted into possible therapeutic effects of this molecule for treatment of autoimmune disorders involving aberrant T cell activation or Ig production.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

We claim:

1. A method for regulating functional CTLA4 positive T cell interactions with B7 positive cells comprising contacting said B7 positive cells with a B7 ligand to interfere with reaction of B7 antigen with CTLA4, wherein said B7 ligand is a fusion protein that contains a portion of the extracellular domain of CTLA4, which portion binds B7.

2. The method of claim 1, wherein said ligand is a CTLA4Ig fusion protein having a first amino acid sequence containing amino acid residues from position 1 to position 125 of the amino acid sequence corresponding to the extracellular domain of CTLA4 and a second amino acid sequence containing amino acid residues corresponding to the hinge, CH2 and CH3 regions of human immunoglobulin Cγ1.

3. The method of claim 1, wherein said B7 positive cells are B cells.

4. The method of claim 1, wherein said ligand is a CD28Ig/CTLA4Ig fusion protein hybrid having a first amino acid sequence corresponding to a portion of the extracellular domain of CD28 receptor, which portion binds B7, fused to a second amino acid sequence corresponding to a portion of the extracellular domain of CTLA4 receptor, which portion binds B7, and a third amino acid sequence corresponding to the hinge, CH2 and CH3 regions of human immunoglobulin Cγ1.

5. A method for treating immune system diseases mediated by T cell interactions with B7 positive cells comprising administering to a subject a B7 ligand to regulate T cell interactions with said B7 positive cells wherein said B7 ligand is a fusion protein that contains a portion of the extracellular domain of CTLA4, which portion binds B7.

6. The method of claim 5, wherein said ligand is CTLA4Ig fusion protein.

7. The method of claim 5, wherein said ligand is a CD28Ig/CTLA4Ig fusion protein hybrid.

8. The method of claim 5, wherein said T cell interactions are inhibited.

* * * * *

UNITED STATES PATENT AND TRADEMARK OFFICE
CERTIFICATE OF CORRECTION

PATENT NO. : 5,434,131

DATED : July 18, 1995

INVENTOR(S) : Linsley et al.

It is certified that error appears in the above-indentified patent and that said Letters Patent is hereby corrected as shown below:

In column 8, line 31, "CDMS" should read --CDM8--;

In column 8, line 56, "MCt061/p3" should read --MC1061/p3--;

In column 9, line 52, "Req." should read --Reg.--;

In column 11, line 33, "altograft" should read --allograft--;

In column 12, line 52, "Milsrein" should read --Milstein--;

In column 15, line 20, "chimetic" should read --chimeric--;

In column 17, line 66, "CDMS" should read --CDM8--;

In column 18, line 3, "CDMS" should read --CDM8--;

In column 18, line 64, "NO:! 1)" should read --NO:11)--;

In column 19, line 10, "OMCTA" should read --OMCTLA--;

In column 20, line 49, delete "DO" after the word --corning--;

In column 21, line 2, delete "which" after the word --using--;

In column 21, line 3, insert --which-- after "supernatant";

In column 22, line 42, "CD2S" should read --CD28--;

UNITED STATES PATENT AND TRADEMARK OFFICE
CERTIFICATE OF CORRECTION

PATENT NO. : 5,434,131

DATED : July 18, 1995

INVENTOR(S) : Linsley et al.

It is certified that error appears in the above-indentified patent and that said Letters Patent is hereby corrected as shown below:

In column 23, line 20, insert --9.3-- after "mAb";

In column 23, line 65, "Staphylococcat" should read --Staphylococcal--.

Signed and Sealed this

Twenty-seventh Day of May, 1997

Attest:

BRUCE LEHMAN

Attesting Officer

Commissioner of Patents and Trademarks